(12) United States Patent
Schepis et al.

(10) Patent No.: US 11,793,443 B2
(45) Date of Patent: Oct. 24, 2023

(54) ADJUSTABLE RANDOM ELECTRICAL STIMULATION TECHNOLOGIES

(71) Applicant: Soin Neuroscience, LLC, Dayton, OH (US)

(72) Inventors: Eric A Schepis, Alpharetta, GA (US); Amol Soin, Dayton, OH (US)

(73) Assignee: Soin Neuroscience, LLC, Dayton, OH (US)

( * ) Notice: Subject to any disclaimer, the term of this patent is extended or adjusted under 35 U.S.C. 154(b) by 0 days.

(21) Appl. No.: 17/984,039

(22) Filed: Nov. 9, 2022

(65) Prior Publication Data
US 2023/0240580 A1 Aug. 3, 2023

Related U.S. Application Data

(60) Provisional application No. 63/305,530, filed on Feb. 1, 2022.

(51) Int. Cl.
A61B 5/00 (2006.01)
A61B 5/291 (2021.01)

(52) U.S. Cl.
CPC ............ A61B 5/291 (2021.01); A61B 5/7264 (2013.01)

(58) Field of Classification Search
CPC ............................. A61B 5/291; A61B 5/7264
See application file for complete search history.

(56) References Cited

U.S. PATENT DOCUMENTS 5,983,141 A 11/1999 Sluijter et al.
7,117,038 B1 10/2006 Overstreet
(Continued)

FOREIGN PATENT DOCUMENTS

CN 101390789 A 3/2009
CN 101583879 A 11/2009
(Continued)

OTHER PUBLICATIONS

International Search Report, European Patent Office, International Patent Application No. PCT/US2018/013700, dated Mar. 19, 2018, 4 pages.
(Continued)

Primary Examiner — Rex R Holmes
(74) Attorney, Agent, or Firm — Taft Stettinius & Hollister LLP

(57) ABSTRACT

A method of providing therapy to a patient according to one embodiment includes partitioning a frequency range into a plurality of discrete frequency bands with each having a corresponding bandwidth, generating a composite electrical signal based on a plurality of periodic signals, wherein each periodic signal has a frequency within a corresponding frequency band of the plurality of discrete frequency bands, delivering the composite electrical signal through one or more electrodes to the patient to target at least one of neural tissue or non-neural tissue of the patient, adjusting an amplitude of one or more of a voltage or a current of the composite electrical signal within a selected frequency band of the plurality of discrete frequency bands to generate an adjusted signal based on feedback received from the patient, and delivering the adjusted electrical signal through the one or more electrodes to provide therapy to the patient.

18 Claims, 16 Drawing Sheets

(56) References Cited

U.S. PATENT DOCUMENTS

| | | | |
|---|---|---|---|
| 10,603,498 B2* | 3/2020 | Blum | A61N 1/36125 |
| 2003/0114886 A1 | 6/2003 | Gluckman et al. | |
| 2006/0149337 A1 | 7/2006 | John | |
| 2006/0161235 A1 | 7/2006 | King | |
| 2007/0060991 A1 | 3/2007 | North et al. | |
| 2007/0142864 A1 | 6/2007 | Libbus et al. | |
| 2008/0077192 A1 | 3/2008 | Harry et al. | |
| 2008/0269836 A1 | 10/2008 | Foffani et al. | |
| 2009/0030476 A1* | 1/2009 | Hargrove | A61N 1/36025 |
| | | | 607/45 |
| 2010/0010556 A1 | 1/2010 | Zhao et al. | |
| 2011/0009919 A1 | 1/2011 | Carbunaru et al. | |
| 2011/0009923 A1 | 1/2011 | Lee | |
| 2011/0144521 A1 | 6/2011 | Molnar et al. | |
| 2011/0201944 A1 | 8/2011 | Higgins et al. | |
| 2012/0059438 A1 | 3/2012 | De Ridder | |
| 2012/0123502 A1 | 5/2012 | Aghassian et al. | |
| 2013/0245486 A1 | 9/2013 | Simon et al. | |
| 2013/0253365 A1 | 9/2013 | Crosson et al. | |
| 2013/0317564 A1 | 11/2013 | Lin et al. | |
| 2014/0031895 A1 | 1/2014 | Rahimi et al. | |
| 2014/0316268 A1 | 10/2014 | Kafiluddi et al. | |
| 2015/0012063 A1 | 1/2015 | Chen | |
| 2015/0157864 A1 | 6/2015 | Rosenberg | |
| 2016/0001083 A1 | 1/2016 | Moffitt et al. | |
| 2016/0199662 A1 | 7/2016 | Wundrich et al. | |
| 2016/0256689 A1 | 9/2016 | Vallejo et al. | |
| 2016/0271413 A1 | 9/2016 | Vallejo et al. | |
| 2017/0001003 A1 | 1/2017 | Pivonka et al. | |
| 2019/0201657 A1 | 7/2019 | Popelka et al. | |
| 2019/0298988 A1 | 10/2019 | Monteiro | |
| 2019/0366097 A1 | 12/2019 | Schepis | |
| 2020/0054879 A1 | 2/2020 | Torgerson | |
| 2020/0139127 A1 | 5/2020 | Zhang et al. | |
| 2020/0164213 A1 | 5/2020 | John | |
| 2020/0353256 A1* | 11/2020 | Vallejo | A61N 1/36171 |
| 2022/0080200 A1 | 3/2022 | Molnar et al. | |
| 2022/0096822 A1 | 3/2022 | Schepis et al. | |
| 2022/0257957 A1 | 8/2022 | Kotchevar et al. | |
| 2022/0288394 A1 | 9/2022 | Bennett et al. | |
| 2023/0074017 A1 | 3/2023 | Pan | |
| 2023/0146551 A1 | 5/2023 | Park et al. | |

FOREIGN PATENT DOCUMENTS

| | | |
|---|---|---|
| EP | 2703042 A1 | 3/2014 |
| JP | 2006204520 A | 8/2006 |
| JP | 2009505689 A | 2/2009 |
| WO | 9318821 A1 | 9/1993 |

OTHER PUBLICATIONS

Written Opinion, European Patent Office, International Patent Application No. PCT/US2018/013700, dated Mar. 19, 2018, 7 pages.
Australian First Examination Report; Australia Patent Office; Australian Patent Application No. 2018210216; dated Aug. 23, 2019; 2 pages.
Canadian Office Action; Canadian Intellectual Property Office; Canadian Patent Application No. 3,048,498; dated Jan. 29, 2020; 5 pages.
Japanese Office Action; Japan Patent Office; Japanese Patent Application No. 2019-538339; dated Dec. 10, 2019; 14 pages.
Korean Office Action; Korean Intellectual Property Office; Korean Patent Application No. 10-2019-7023751; dated Nov. 14, 2019; 4 pages.
New Zealand First Examination Report; New Zealand Intellectual Property Office; New Zealand Patent Application No. 756351; dated Feb. 10, 2020; 3 pages.
International Search Report; International Searching Authority; International Application No. PCT/US2023/011998; dated Apr. 12, 2023; 2 pages.
Written Opinion of the International Searching Authority; International Searching Authority; International Application No. PCT/US2023/011998; dated Apr. 12, 2023; 9 pages.
Canadian Examination Report; Canadian Intellectual Property Office; Canadian Patent Application No. 3,048,495; dated Aug. 10, 2020; 5 pages.
Chinese Office Action; China National Intellectual Property Administration; Chinese Patent Application No. 201880007499.5; dated Oct. 10, 2022; 7 pages.
Indian Examination Report; Intellectual Property India; Indian Patent Application No. 201917031620; dated Jan. 27, 2021; 5 pages.
Japanese Office Action; Japan Patent Office; Japanese Patent Application No. 2019-538339; dated Sep. 1, 2020; 7 pages.
New Zealand Second Examination Report; New Zealand Intellectual Property Office; New Zealand Patent Application No. 756351; dated Jul. 14, 2020; 4 pages.
New Zealand Third Examination Report; New Zealand Intellectual Property Office; New Zealand Patent Application No. 756351; dated Nov. 3, 2020; 1 page.

* cited by examiner

ADJUSTABLE RANDOM ELECTRICAL STIMULATION TECHNOLOGIES

CROSS-REFERENCE TO RELATED APPLICATION

This application claims priority to and the benefit of U.S. Provisional Application No. 63/305,530, titled "Adjustable Random Electrical Stimulation Technologies," filed on Feb. 1, 2022, the contents of which are incorporated herein by reference in their entirety.

TECHNICAL FIELD

The technology described herein generally relates to providing therapy to a patient via the application of adjustable random electrical stimulation.

BACKGROUND

Periodic electrical waveforms are commonly used to stimulate nervous tissue to treat patients with neurological disorders. Fourier's theorem teaches that those periodic waveforms (i.e., pulses) are composed of sinusoidal signals that are harmonically related to the repetition frequency of the original signal. "Harmonically related" means that the frequency of the sinusoids is an integral multiple of some "basic" or "fundamental" number. That is, the frequency is one times, two times, three times, etc. the basic or fundamental number. Each of the component frequencies is known as a harmonic, and, collectively, these component frequencies are known as the Fourier series. The amplitude of each harmonic is correlated to the amplitude of the fundamental frequency.

Altogether, the electrical stimulation waveforms that are used today limit stimulation energy to the harmonic frequencies of the periodic signal, and do not deliver energy at frequencies between the harmonic frequencies or at frequencies that are less than the fundamental frequency. Moreover, they do not enable independent control of the energy content of any frequency within its spectrum. For example, periodic biphasic square-wave pulses are used to stimulate nervous tissue to treat pain, motor, and sensory disorders. The Fourier series of a biphasic square-wave pulse includes the fundamental frequency, and its odd multiples (i.e., it does not have even numbered harmonics). The amplitude of each harmonic is represented as 1/integral multiple of the fundamental frequency's (i.e., 1, 3, 5, 7, 9) amplitude. That is, constant-voltage biphasic square-wave pulses delivered at 200 Hertz (Hz) and 1 volt (V) has a fundamental frequency (amplitude) of 200 Hz (1/1 V) and harmonics at 600 Hz (1/3 V)), 1000 Hz (1/5 V), 1400 Hz (1/7 V), and 1800 Hz (1/9 V), etc. This stimulation waveform does not deliver energy at frequencies that are less than 200 Hz (fundamental frequency) or between harmonics (e.g., between 200 Hz and 600 Hz; between 600 Hz and 1000 Hz; between 1000 Hz and 1400 Hz, etc.), and the energy content delivered in each harmonic is fixed to that of the fundamental frequency and cannot be independently modulated (i.e., deliver 1 V at 1000 Hz and 1/3 V at 200 Hz).

An electrical stimulation therapy that delivers a waveform that is flexible in both frequency and power would better accommodate for patient variability and disease state, ultimately leading to better patient outcomes. Moreover, a random waveform would help prevent neurological tolerance, which is a phenomenon that plagues long-term efficacy of periodic stimulation waveforms.

SUMMARY

One embodiment is directed to a unique system and methods for providing therapy to a patient using adjustable random electrical stimulation. Other embodiments are directed to apparatuses, systems, devices, hardware, methods, and combinations thereof for providing therapy to a patient using adjustable random electrical stimulation.

According to an embodiment, a method for providing therapy to a patient may include partitioning a frequency range into a plurality of discrete frequency bands, each of the discrete frequency bands having a corresponding bandwidth, generating, by at least one signal generator controlled by a controller of an electrical stimulation system, a composite electrical signal based on a plurality of periodic signals, wherein each periodic signal has a frequency within a corresponding frequency band of the plurality of discrete frequency bands, delivering the composite electrical signal through one or more electrodes to the patient to target at least one of neural tissue or non-neural tissue of the patient, adjusting an amplitude of one or more of a voltage or a current of the composite electrical signal within a selected frequency band of the plurality of discrete frequency bands to generate an adjusted electrical signal based on feedback received from the patient, and delivering the adjusted electrical signal through the one or more electrodes to provide therapy to the patient.

In some embodiments, generating the composite electrical signal based on the plurality of periodic signals may include incorporating randomness into one or more of the plurality of periodic signals.

In some embodiments, incorporating randomness into one or more of the plurality of periodic signals may include randomizing a corresponding frequency of each of the plurality of periodic signals within the corresponding bandwidth.

In some embodiments, incorporating randomness into one or more of the plurality of periodic signals may include randomizing a corresponding amplitude of each of the plurality of periodic signals within the corresponding bandwidth.

In some embodiments, incorporating randomness into one or more of the plurality of periodic signals may include randomizing a corresponding phase of each of the plurality of periodic signals within the corresponding bandwidth.

In some embodiments, each of the plurality of periodic signals may be embodied as or include a sinusoidal waveform.

In some embodiments, generating the composite electrical signal based on the plurality of periodic signals may include generating the composite electrical signal as a Fourier series based on the plurality of periodic signals.

In some embodiments, generating the composite electrical signal based on the plurality of periodic signals may include applying filtration to each of the plurality of periodic signals.

In some embodiments, adjusting the amplitude of the one or more of the voltage or current of the composite electrical signal within the selected frequency band may include amplifying the amplitude of the one or more of the voltage or current of the composite electrical signal within the selected frequency band.

In some embodiments, adjusting the amplitude of the one or more of the voltage or current of the composite electrical signal within the selected frequency band may include attenuating the amplitude of the one or more of the voltage or current of the composite electrical signal within the selected frequency band.

In some embodiments, adjusting the amplitude of the one or more of the voltage or current of the composite electrical signal within the selected frequency band may include adjusting the amplitude of the one or more of the voltage or current of the composite electrical signal within a first frequency band of the plurality of discrete frequency bands to generate a first adjusted electrical signal based on first feedback received from the patient, and the method may further include adjusting an amplitude of the one or more of the voltage or current of the adjusted electrical signal within a second frequency band of the plurality of discrete frequency bands to generate a second adjusted electrical signal based on second feedback received from the patient.

In some embodiments, the feedback received from the patient may be patient self-report regarding the therapy delivered to the patient.

In some embodiments, the feedback may be based on data generated by one or more sensors of the electrical stimulation system, wherein the one or more sensors measure one or more physiological outcomes of the patient.

In some embodiments, the feedback may include data received from a machine learning system.

In some embodiments, the method may further include executing the machine learning algorithm to identify an adjusted electrical stimulation signal to be delivered through the one or more electrodes to provide therapy to the patient based on a plurality of machine learning inputs.

In some embodiments, the machine learning inputs may include one or more of adjusted electrical stimulation signatures, patient information, patient demographics, diagnosis information, electrode positioning, patient sensations, measure of treatment efficacy or outcomes, time of day, duration of treatment, or time elapsed since start of treatment plan.

In some embodiments, the method may further include placing the one or more electrodes on the patient percutaneously or transcutaneously.

In some embodiments, at least one of the one or more electrodes may be implantable.

In some embodiments, each of the discrete frequency bands may have the same bandwidth.

In some embodiments, the frequency range may be 0 Hz to 25 kHz, and each of the discrete frequency bands in the frequency range of 0 Hz to 25 kHz may have a bandwidth of one of 1 kHz or 2 kHz.

In some embodiments, each of the discrete frequency bands may be an octave band.

In some embodiments, each of the octave bands may be one of a base-2 octave band or a base-10 octave band.

In some embodiments, the frequency range may be 0 Hz to 100 kHz.

In some embodiments, the frequency range may be 0 Hz to 500 kHz.

In some embodiments, the frequency range may be 0 Hz to 2 kHz, and each of the discrete frequency bands in the frequency range of 0 Hz to 2 kHz may have a bandwidth of 200 Hz.

In some embodiments, the frequency range may be 1 kHz to 100 kHz.

In some embodiments, the frequency range may be 100 kHz to 1 MHz.

According to another embodiment, a system for providing therapy to a patient may include an electrode, a signal generator coupled to the electrode, and a controller. The controller may instruct the signal generator to (i) generate a composite electrical signal based on a plurality of periodic signals, wherein a frequency range is partitioned into a plurality of discrete frequency bands, each of the discrete frequency bands having a corresponding bandwidth, and wherein each periodic signal has a frequency within a corresponding frequency band of the plurality of discrete frequency bands, (ii) deliver the composite electrical signal through the electrode to the patient to target at least one of neural tissue or non-neural tissue of the patient, (iii) adjust an amplitude of one or more of a voltage or a current of the composite electrical signal within a selected frequency band of the plurality of discrete frequency bands to generate an adjusted electrical signal based on feedback received from the patient, and (iv) deliver the adjusted electrical signal through the electrode to provide therapy to the patient.

This summary is not intended to identify key or essential features of the claimed subject matter, nor is it intended to be used as an aid in limiting the scope of the claimed subject matter. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

DETAILED DESCRIPTION

Figure 1:
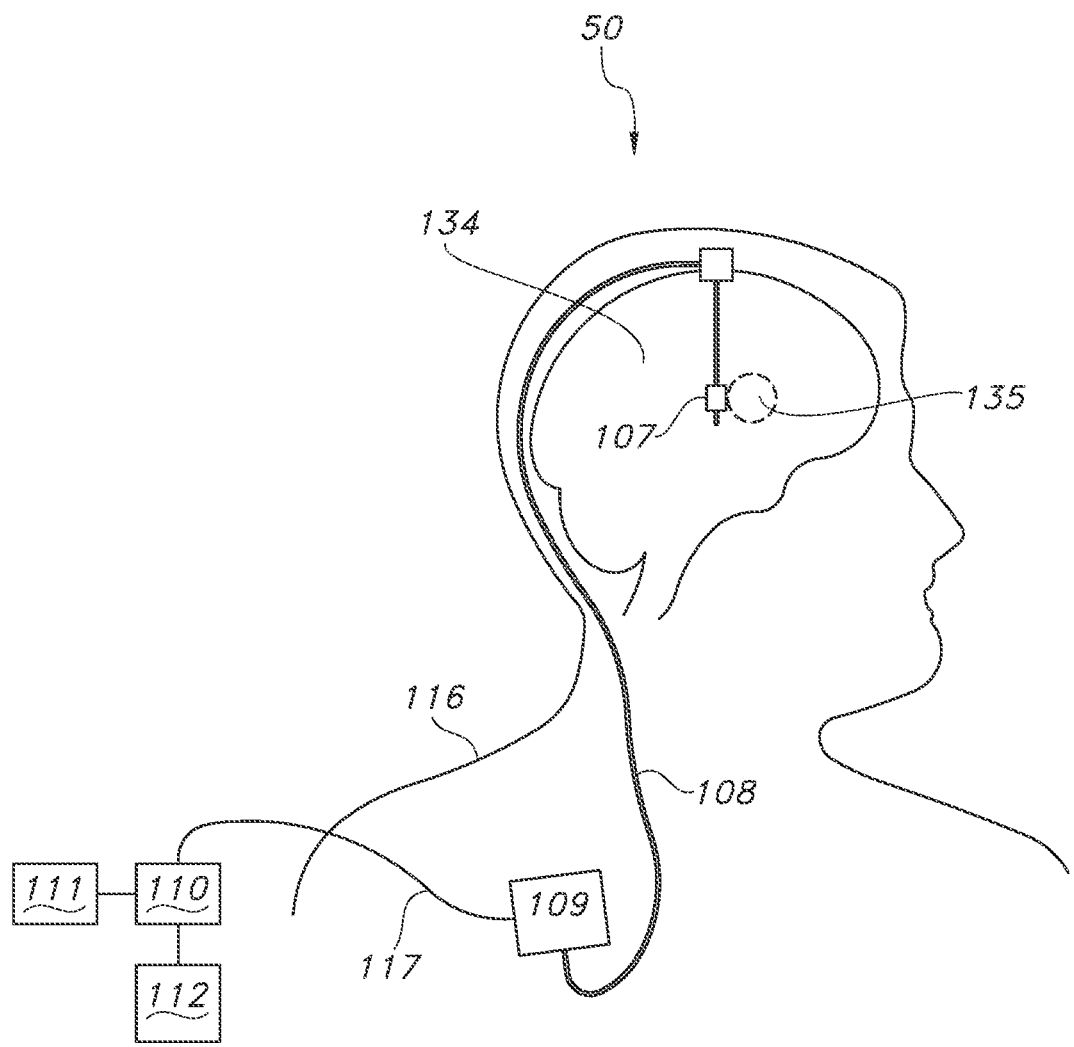
FIG. 1 illustrates at least one embodiment of a system for delivering one or more electrical signals to target neural tissue, non-neural tissue, or a combination thereof in a patient, where the electrical signals are adjustable, and where the target tissue is located within or adjacent to the patient's brain.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

It should be appreciated that the technologies described herein involve a system and method to modulate neural and non-neural activity with an electrical therapy that is flexible in both frequency and power. In particular, in some embodiments, the therapy may be synthesized by a plurality of randomly-varying, sinusoidal (or otherwise periodic), waveform signals that drive an electrical signal generator. The signal generator may compile the plurality of signals into a single composite waveform and deliver the waveform (e.g., voltage or current) through one or more electrodes to the patient. This is efficiently done with sinusoidal waveform, for example, because the frequency content of a sinusoidal waveform is composed of a single frequency (i.e. 1/period). However, similar concepts apply for other periodic signals composed of multiple harmonic frequencies (e.g., squarewaves, pulses, etc.). In such embodiments, the system may include filtration to further control the spectra of stimulation signals as described herein. Moreover, the power at each frequency band may be adjusted by the subject based on feedback (e.g., patient self-report, closed-loop via sensors or recordings of physiological activity, artificial intelligence, etc.). As such, the resultant power spectrum may have one or more local maxima and minima, and be unique to each person.

The therapy may be generated by an external or implantable electrical stimulator and delivered through electrodes to the patient's brain or spinal cord, a dorsal root ganglion, a sympathetic nerve or chain ganglion, a cranial nerve, a parasympathetic nerve, or a peripheral nerve.

The therapy may be used to treat pain (e.g., chronic pain), an autonomic disorder (e.g., diabetic peripheral neuropathy, hypertension, hypotension, complex regional pain syndrome (CRPS), Raynaud's syndrome, overactive bladder, urinary incontinence, fecal incontinence, fecal constipation, migraine, etc.), a sensory disorder (e.g., tinnitus, hearing loss, vertigo, etc.), a motor disorder (e.g., Huntington's disease, Parkinson's disease, Multiple Sclerosis, spinal muscular atrophy (SMA), dystonia, essential tremor, etc.), or a combination thereof. Further, the therapy provided to the patient can elicit plastic changes in neural tissue, non-neural tissue, or a combination thereof to mitigate or abolish a pathophysiologic disease or syndrome. Plastic changes are changes to the neural tissue, non-neural tissue, or a combination thereof in response to physiological demands. Such plastic changes can include morphological and functional changes.

The adjustable electrical stimulation signal enables independent tuning or adjustment of the energy content within all frequencies of its frequency spectrum, for example, as described in further detail below. As such, the power spectrum of the adjusted electrical stimulation signal may have one or more local maxima and/or one or more local minima. Local maxima may be in neighboring bandwidths or separated by one or more frequency bands. Similarly, local minima may be in neighboring bandwidths or separated by one or more frequency bands. The electrical power described as local maxima and local minima may interact and cause more effective, safer, and power efficient therapies.

In some embodiments, one or more electrical signals can be adjusted based on patient feedback by adjusting energy contained within a frequency band, while in other embodiments, the electrical signals can be adjusted based on patient feedback by adjusting a phase component of the electrical signal. For example, one or more electrodes can be implanted, inserted percutaneously, or positioned transcutaneously such that the electrodes are nearby the target neural tissue, non-neural tissue and combination thereof as necessary to treat their disease or syndrome. A signal generator can then be instructed to deliver one or more electrical signals through the one or more electrodes. The patient and/or caregiver can then "program" the optimal stimulation waveform by operating a controller. The controller can adjust the waveform associated with the electrical signal(s) being delivered to the patient by adjusting energy levels within a particular frequency band, and for all frequency bands delivered, to best treat the patient.

For example, the controller can divide/partition a frequency range into a series of frequency bands, with each of the frequency bands being associated with a different sinusoidal waveform or other periodic signal, and adjust a composite waveform (formed from the plural sinusoids/periodic signals) by amplifying or attenuating the power within an individual frequency band or combinations of frequency bands until patient feedback indicates an optimal therapeutic benefit. In another embodiment, rather than amplifying or attenuating the power with the frequency band, the controller may shift the phase components of the signal within the frequency band to adjust the electrical signal for therapeutic benefit. The controller can adjust the electrical signals while the patient is stationary or active, and with feedback from the user. In another embodiment, multiple signal generators may be driven by the controller to simultaneously power individual frequency bands as described herein.

The adjustability feature contemplated by the technologies described herein allows for the therapy provided to the patient to be tuned, altered, adjusted, etc. based on feedback received from the patient, the specific symptoms or disease state being treated, the physical characteristics of the patient, the mental characteristics of the patient, and/or the current activity level of the patient, where each of these variables can affect how the electrical signal(s) provide therapeutic benefit to the patient. Feedback can be provided by the patient based on self-report (e.g., introspection, observations of unwanted sensory- and/or motor activity, autonomic dysfunction, etc.), determined from data generated by sensors measuring physiological outcomes, based on data from artificial intelligence or machine learning systems (e.g., output or feedback data), or based on combinations thereof.

In some embodiments, the electrical signal(s) can be adjusted based on patient feedback describing unwanted sensations. Examples of unwanted sensations include pain and other sensations, such as urinary urgency and fecal urgency. Other examples include unwanted sensations of touch, vibration, pressure, tightness, feelings of warmth or cold, numbness, sounds of ringing (or buzzing, hissing, clicking, roaring, humming), anxiety, dizziness, aura, loss of sound intensity, and/or loss of sound quality. Any of the unwanted sensations described above can occur in the absence of an external stimulus and/or when the patient is perfectly still.

In some embodiments, the electrical signal(s) can be adjusted based on patient feedback describing physiological outcomes. It should be appreciated that the physiological outcomes may be reported by the patient, observed by a clinician, evaluated based on data generated by one or more sensors, and/or otherwise determined depending on the particular embodiment. Examples of physiological outcomes that can be used to adjust the electrical signals include those pertaining to bladder and bowel function, such as incontinence, constipation, voided volumes, voiding pressures, voiding frequency, and electromyogram signals of the urinary and colonic ensemble. Other examples of physiological outcomes that can be used to adjust the electrical signals include those pertaining to motor function, such as electromyogram signals, strength, weakness, stiffness, spasm, contracture, tremors, spasticity, atrophy, bradykinesia, and paralysis. Other markers of physiological activity that could be used to adjust the electrical signals include electroencephalogram signals, evoked brain potentials, and cognitive changes including dementia, hallucination, and delusion. Markers of autonomic function can also be used to adjust the electrical signals, such as heart-rate, blood flow, blood pressure, respiration, nausea, sweat production, skin color, and edema. Any of the physiological changes described above can be used to adjust the electrical signals in the absence of an external stimulus or when the patient is perfectly still. In some embodiments, sensor types include biopotential electrodes, pressure sensors and flow meters, chemical sensors, and/or temperature sensors (e.g., thermistors). It should be appreciated that, in some embodiments, one or more of the sensors can act in a close-loop fashion to adjust the electrical signals to provide and optimize therapy.

Whether the electrical signal(s) are being applied to target neural tissue, non-neural tissue, or a combination thereof located within or adjacent the patient's brain or spinal cord, a dorsal root ganglion, a sympathetic chain ganglion, a cranial nerve, autonomic circuitry, or a peripheral nerve, the technologies described herein illustrate that the specific parameters of the electrical signals and the location of the electrodes through which electrical signals is delivered can be selectively controlled to provide improved symptom relief and therapy to the patient for the treatment of pain, autonomic disorders, sensory disorders, motor disorders, etc. The specific system and parameters are discussed in more detail below.

Referring now to FIG. 1, there is illustrated a system 50 for delivering one or more electrical signals to provide therapy to a patient 116, where the target neural tissue, non-neural tissue, or a combination thereof 135 is located within or adjacent tissue within the patient's brain 134. In general, the system 50 in FIG. 1 can include one or more electrodes 107 (shown diagrammatically in FIG. 1 and not in any specific detail) that are connected by an electrical lead 108 to a signal generator 109. In various embodiments, one or more electrodes 107 (or electrical contacts) may be embodied on, form a portion of, or be electrically coupled to one or more electrical leads 108 that are electrically (or electromagnetically) coupled to the signal generator 109. An additional lead 117 can be used to couple the signal generator 109 to the rest of the system 50, which can include a user interface 112 and a controller 110, where it is to be understood that as an alternative to the use of the lead 117, the signal generator 109 can be wirelessly connected to the rest of the system 50. The system can also include a power system 111 and/or a patient monitor system. Further, it should be understood that while the system 50 of FIG. 1 illustrates a configuration where electrical signals can be delivered to target neural tissue, non-neural tissue, or a combination 135 thereof utilizing an electrode 107 coupled to an implantable signal generator 109 via a lead 108, the electrode 107 can alternatively be coupled to an external signal generator via a wireless antenna system. In addition, in some embodiments, more than one electrode 107 can be used. Regardless of the exact type (e.g., percutaneous, transcutaneous, implantable, etc.) or configuration (e.g., monopolar, bipolar, multipolar, etc.) of the electrode(s) 107, the electrode(s) 107 can be in the form of an electrode assembly that can deliver electrical signals to a patient to provide therapy to the patient and/or improve one or more of the patient's symptoms. Specific diseases or conditions that can be treated based on stimulation of the brain include, for example, Parkinson's disease, essential tremor, depression, obsessive compulsive disorder, Tourette's syndrome, epilepsy, schizophrenia, narcolepsy, seizures, Alzheimer's disease, tinnitus, Meniere's disease, and chronic pain.

Figure 2:
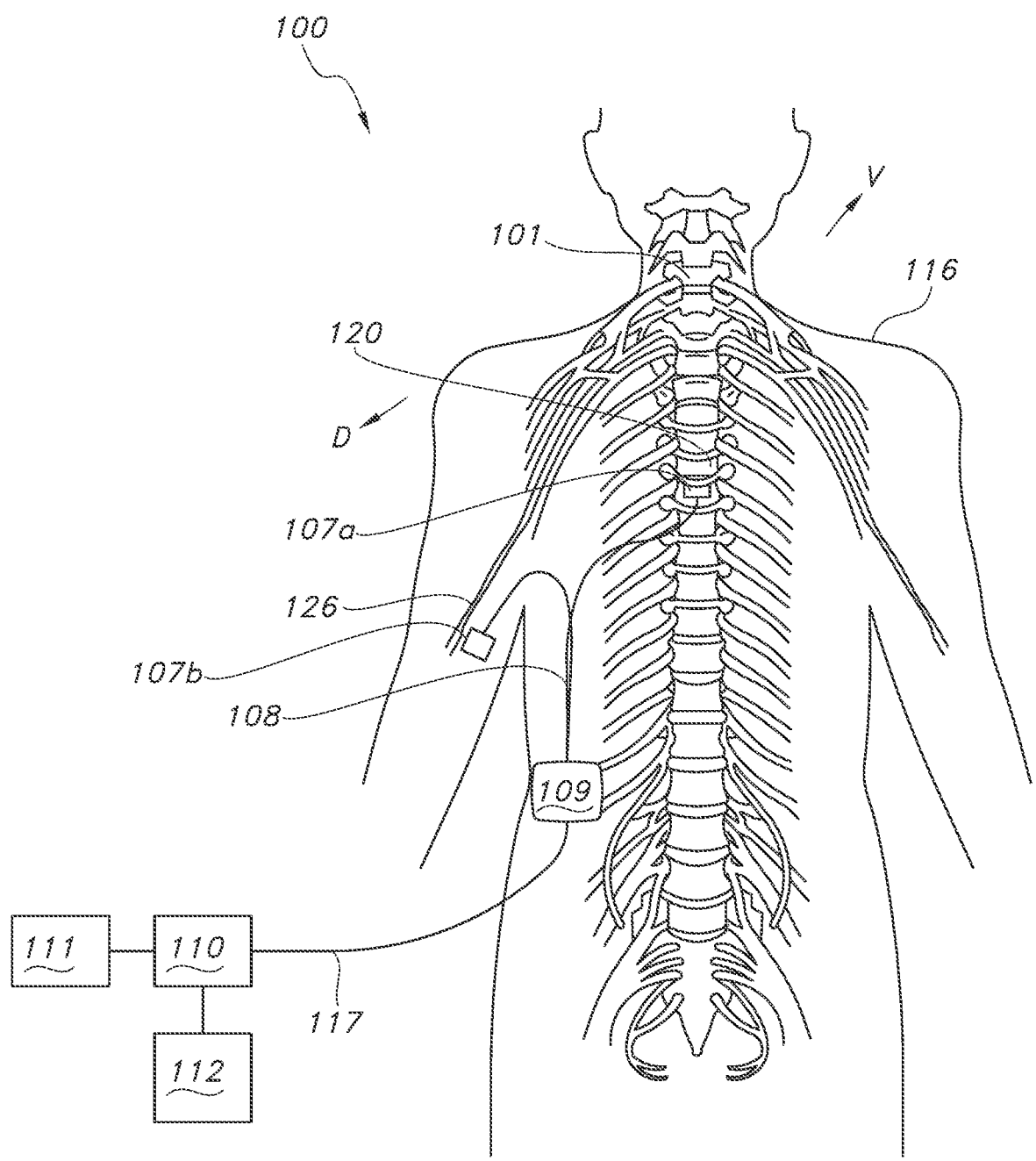
FIG. 2 illustrates at least one embodiment of a system for delivering one or more electrical signals to target neural tissue, non-neural tissue, or a combination thereof in a patient, where the electrical signals are adjustable, and where the target tissue is located within or adjacent the spinal cord.

Referring now to FIG. 2, there is illustrated a system 100 for delivering one or more electrical signals to provide therapy to a patient, where the target neural tissue, non-neural tissue, or a combination thereof is located within or adjacent the spinal cord 101 of a patient 116. As shown in FIG. 2, the system 100 can include multiple devices to control and deliver electrical signals to one or more areas of target neural tissue, non-neural tissue, or a combination thereof located within or adjacent the spinal cord 101 to provide therapy to a patient 116. In general, the system 100 in FIG. 2 can include one or more electrodes 107a and/or 107b (shown diagrammatically in FIG. 2 and not in any specific detail) that are connected by one or more electrical leads 108 to a signal generator 109. An additional lead 117 can be used to couple the signal generator 109 to the rest of the system 100, which can include a user interface 112 and a controller 110, where it is to be understood that as an alternative to the use of the lead 117, the signal generator 109 can be wirelessly connected to the rest of the system 50. The system can also include an isolated power system 111 and/or a patient monitor system. Further, it should be understood that while the system 100 of FIG. 2 illustrates a configuration where electrical signals can be delivered to target neural tissue, non-neural tissue, or a combination thereof utilizing electrodes 107a and/or 107b coupled to an implantable signal generator 109 via a lead 108, the electrodes 107a and/or 107b can alternatively be coupled to an external signal generator via a wireless antenna system. Regardless, the electrodes 107a and/or 107b can be in the form of an electrode assembly that can deliver electrical signals to a patient to provide therapy to the patient and/or improve one or more of the patient's symptoms based on the specific location of the electrodes, as discussed in more detail in FIGS. 3-7 below.

Figure 3:
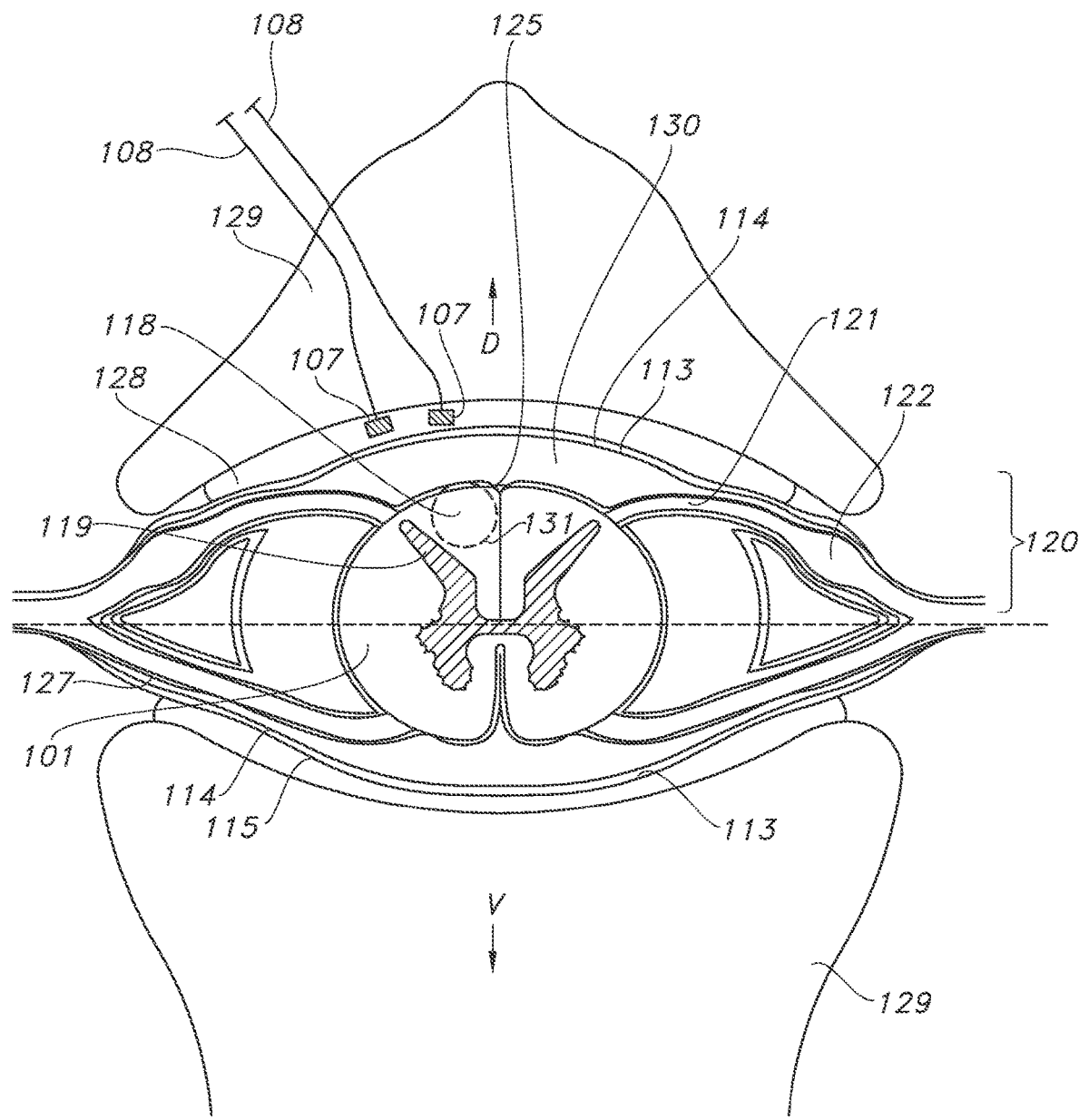
FIG. 3 is a zoomed-in view of the spinal cord and illustrates at least one option for electrode placement according to the system of FIG. 2, where the target tissue is located within or adjacent a dorsal region of the spinal cord, such as the dorsal columns.

Referring now to FIG. 3, the placement of the electrode or electrodes 107 in order to deliver one or more electrical signals to an area within or adjacent target neural tissue, non-neural tissue, or a combination thereof 131 located adjacent a dorsal region 120 of the spinal cord 101, and in particular a dorsal column 118, is discussed in more detail, where the dorsal D and ventral V directions of the spinal cord 101 are labeled for reference purposes. For instance, one or more electrodes 107 can be positioned within a portion of the epidural space 128 of the patient 116 adjacent a dorsal region 120 of the spinal cord 101, where the dorsal region 120 of the spinal cord 101 can be identified via locating the posterior median sulcus 125. As shown, the epidural space 128 is positioned between the bone 129 (vertebrae) and the dura mater 115. Thus, electrical signals transmitted by the electrode 107 must be configured to pass through the dura mater 115, subdural cavity 113, arachnoid mater 114, subarachnoid cavity 130, and pia mater 127 to reach the target neural tissue, non-neural tissue, or a combination thereof 131 and deliver the desired electrical signals therein. By placing the electrode or electrodes 107 in the epidural space 128 adjacent a dorsal region 120 of the spinal cord 101, electrical signals can be delivered to target neural tissue, non-neural tissue, or a combination thereof 131 located within or adjacent a dorsal column 118 to provide therapy to the patient. It is also to be understood that the electrode or electrodes 107 can be positioned in any suitable location in the dorsal region 120 of the spinal cord 101 in order to deliver electrical signals to an area within or adjacent other target neural tissue, non-neural tissue, or a combination thereof, such as tissue located adjacent a dorsal horn 119 or a dorsal root 121. Specific diseases or conditions that can be treated based on stimulation of the dorsal region of the spinal cord, and in particular, the dorsal columns include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 4:
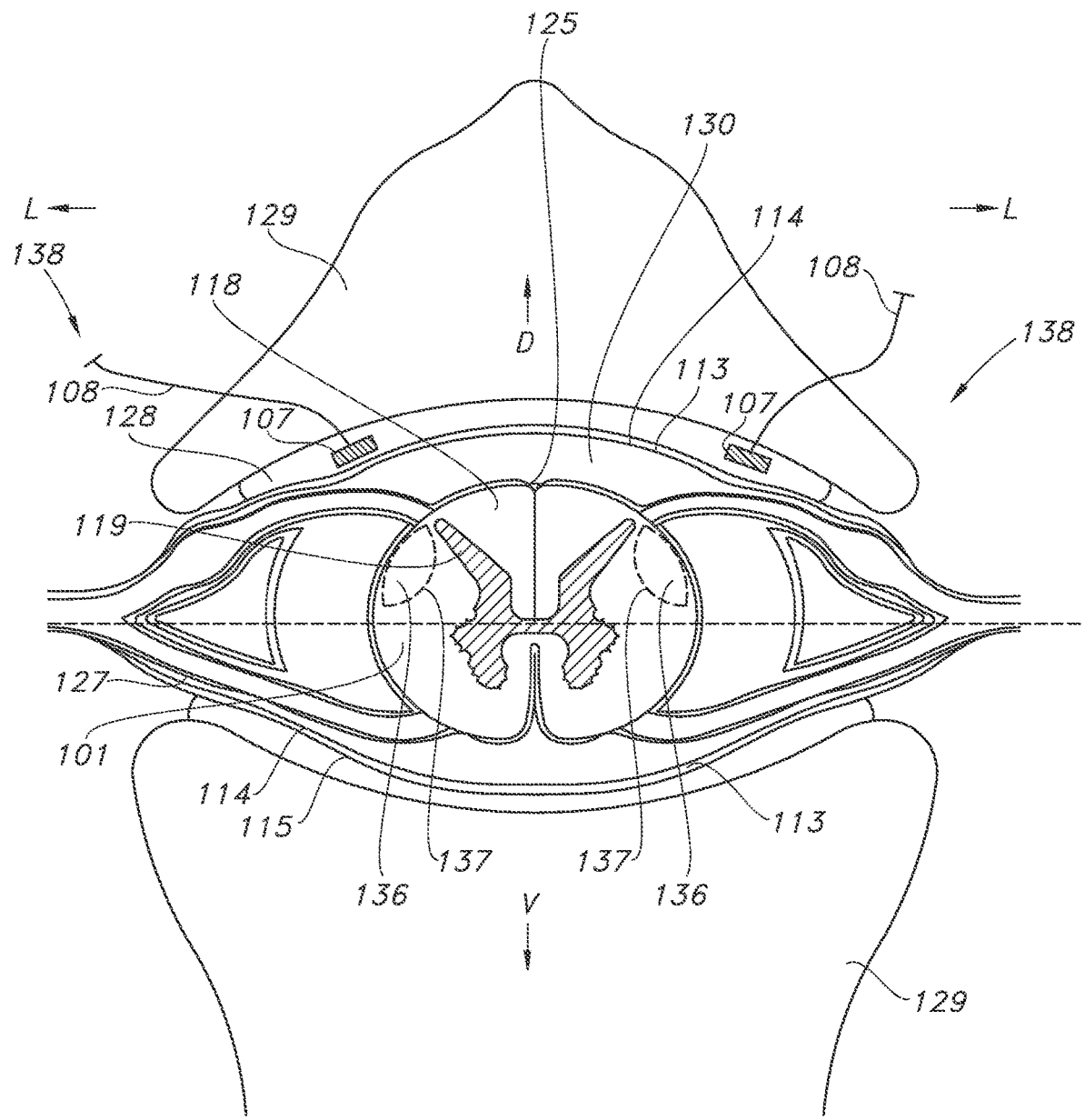
FIG. 4 is a zoomed-in view of the spinal cord and illustrates at least one other option for electrode placement according to the system of FIG. 2, where the target tissue is located within or adjacent to the dorsolateral region of the spinal cord, such as the dorsolateral *funiculus*.

Referring now to FIG. 4, the placement of the electrode or electrodes 107 in order to deliver one or more electrical signals to an area within or adjacent target neural tissue, non-neural tissue, or a combination thereof 137 located in a dorsolateral region 138 of the spinal cord 101 is discussed in more detail, where the dorsal D, ventral V, and lateral L directions are labeled for reference purposes. For instance, one or more electrodes 107 can be positioned adjacent a dorsolateral region 138 of the spinal cord 101. By placing the electrode or electrodes 107 adjacent a dorsolateral region 138 of the spinal cord 101, electrical signals can be delivered to target neural tissue, non-neural tissue, or a combination thereof 137 located within or adjacent a dorsolateral region 138 of the spinal cord 101 to provide therapy to the patient. Specifically, nerve fiber activity in the right or left dorsolateral *funiculus* 136 or a combination thereof can be altered via electrical signals in order to treat or alleviate symptoms associated various conditions. Specific diseases or conditions that can be treated based on stimulation of the dorsolateral region of the spinal cord, and in particular, the dorsolateral *funiculus* include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 5:
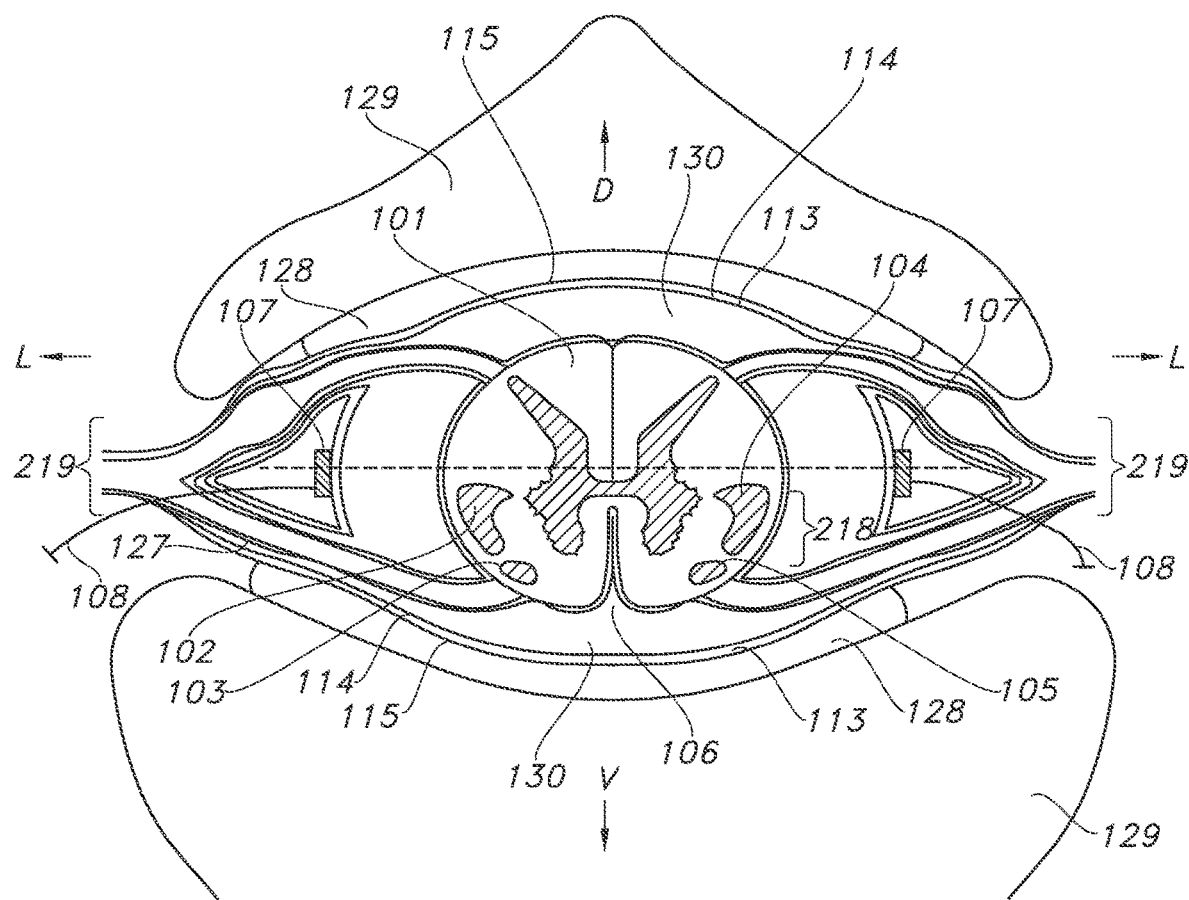
FIG. 5 is a zoomed-in view of the spinal cord and illustrates at least one other option for electrode placement according to the system of FIG. 2, where the target tissue is located within or adjacent the lateral region of the spinal cord, such as the spinothalamic tract.

Referring now to FIG. 5, the placement of the electrode or electrodes 107 in order to deliver one or more electrical signals to an area within or adjacent target neural tissue, non-neural tissue, or a combination thereof 218 located in a lateral region 219 of the spinal cord 101 is discussed in more detail, where the dorsal D, ventral V, and lateral L directions are labeled for reference purposes. For instance, one or more electrodes 107 can be positioned adjacent a lateral region 219 of the spinal cord 101. By placing the electrode or electrodes 107 adjacent lateral region 219 of the spinal cord 101, electrical signals can be delivered to target neural tissue, non-neural tissue, or a combination thereof 218 located within or adjacent a lateral region 219 of the spinal cord 101 to provide therapy to the patient. Specifically, nerve fiber activity in the right lateral spinothalamic tract 102, the left lateral spinothalamic tract 104, or a combination thereof can be altered via electrical signals in order to treat or alleviate symptoms associated various conditions. Moreover, it is to be understood that nerve fiber activity in the right anterior spinothalamic tract 103, the left anterior spinothalamic tract 105, or a combination thereof can also be altered via electrical signals based on the specific positioning of the one or more electrodes 107. Specific diseases or conditions that can be treated based on stimulation of the lateral region of the spinal cord, and in particular, the lateral spinothalamic tract include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain, and fibromyalgia.

Figure 6:
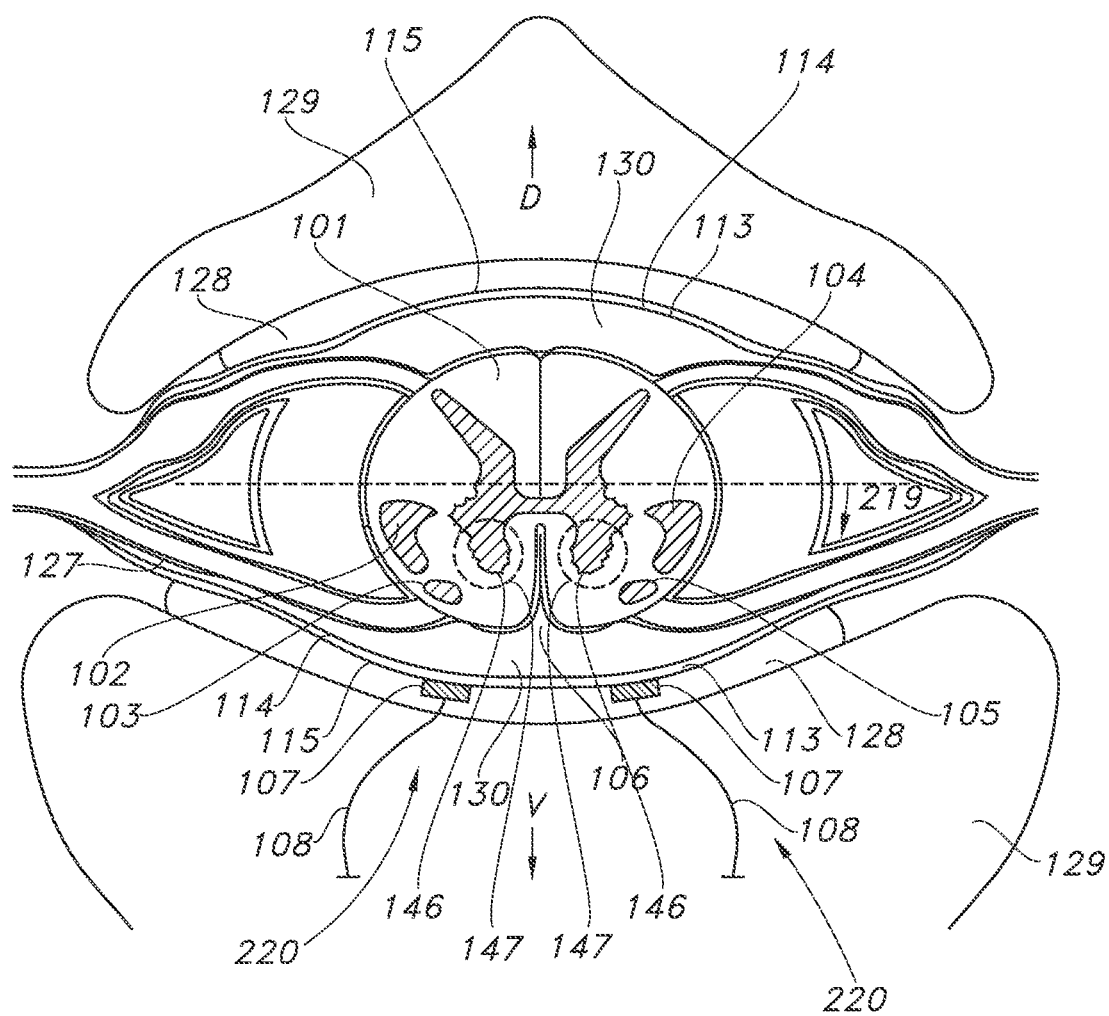
FIG. 6 is a zoomed-in view of the spinal cord and illustrates at least one other option for electrode placement according to the system of FIG. 2, where the target tissue is located with or adjacent the ventral region of the spinal cord, such as the ventral horn.

Referring now to FIG. 6, the placement of the electrode or electrodes 107 in order to deliver one or more electrical signals to an area within or adjacent target neural tissue, non-neural tissue, or a combination thereof 147 located in a ventral region 220 of the spinal cord 101 is discussed in more detail, where the dorsal D and ventral V directions are labeled for reference purposes. For instance, one or more electrodes 107 can be positioned within a portion of the epidural space 128 of the patient 116 adjacent a ventral region 220 of the spinal cord 101, where the ventral region 220 of the spinal cord 101 can be identified via locating the anterior median fissure 106. As shown, the epidural space 128 is positioned between the bone 129 (vertebrae) and the dura mater 115. Thus, electrical signals transmitted by the electrode 107 must be configured to pass through the dura mater 115, subdural cavity 113, arachnoid mater 114, subarachnoid cavity 130, and pia mater 127 to reach the target neural tissue, non-neural tissue, or a combination thereof 147 and deliver the desired electrical signals therein. By placing the electrode or electrodes 107 in the epidural space 128 adjacent a ventral region 220 of the spinal cord 101, electrical signals can be delivered to target neural tissue, non-neural tissue, or a combination thereof 147 located in a ventral region 220 of the spinal cord 101 to provide therapy to the patient. Specifically, in one particular embodiment, nerve fiber activity in the right or left ventral horn 146 or a combination thereof can be altered via electrical signals in order to treat or alleviate symptoms associated various conditions. Specific diseases or conditions that can be treated based on stimulation of the ventral region of the spinal cord include, for example, motoneuron disease (amyotrophic lateral sclerosis; progressive muscular atrophy; progressive bulbar palsy; primary lateral sclerosis; hereditary spastic paraplegia), spinal muscular atrophy (infantile and juvenile spinal muscular atrophy; focal amyotrophy), and multiple sclerosis.

Figure 7:
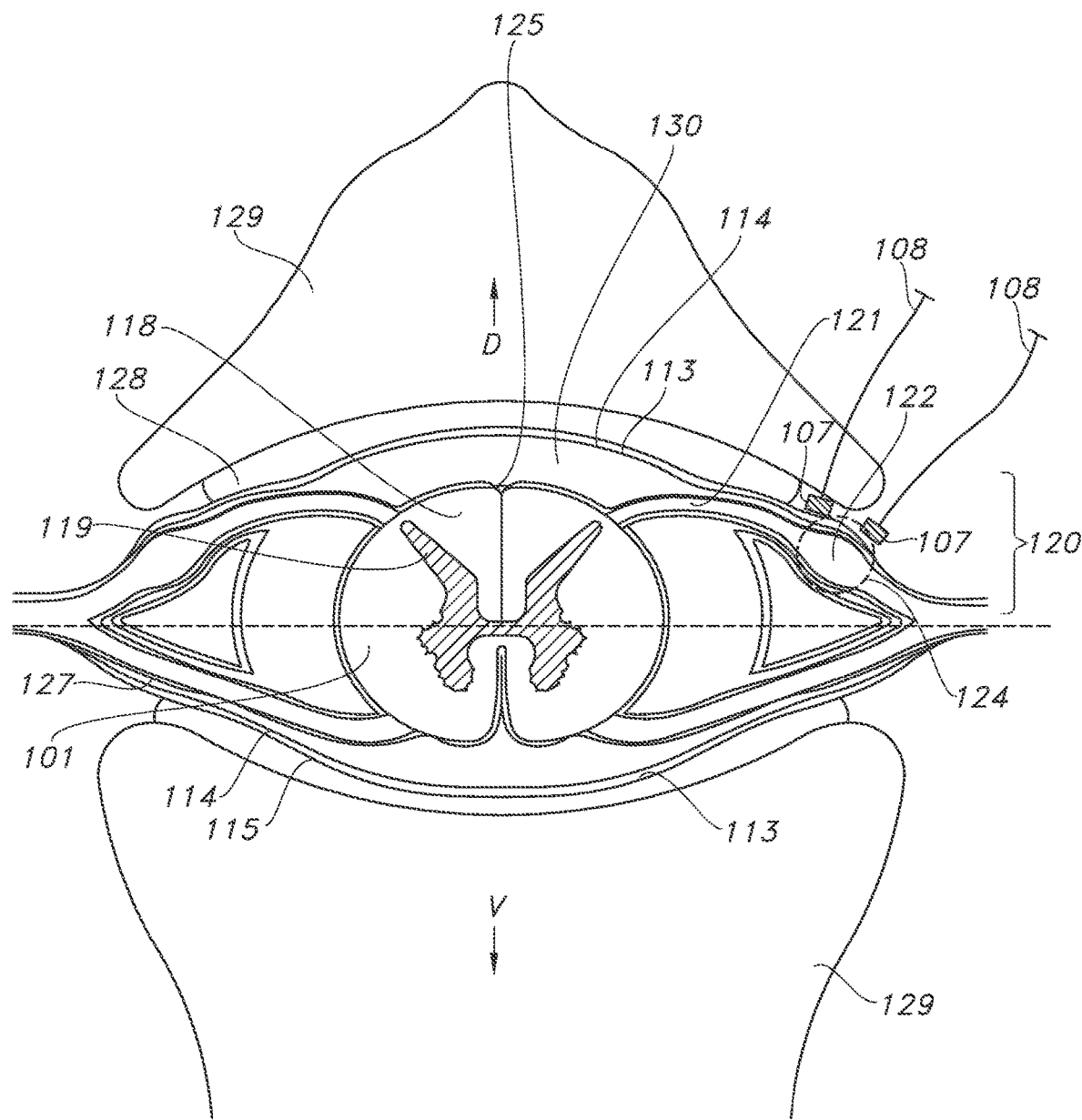
FIG. 7 is a zoomed-in view of the spinal cord and illustrates at least one other option for electrode placement according to the system of FIG. 2, where the target tissue is located within or adjacent a dorsal root ganglion.

Referring now to FIG. 7, the placement of the electrode or electrodes 107 in order to deliver one or more electrical signals to an area within or adjacent target neural tissue, non-neural tissue, or a combination thereof 124 located adjacent or near a dorsal region 120 of the spinal cord 101, and in particular a dorsal root ganglion 122, is discussed in more detail, where the dorsal D and ventral V directions of the spinal cord 101 are labeled for reference purposes. For instance, one or more electrodes 107 can be positioned within a portion of the epidural space 128 of the patient 116 adjacent a dorsal (or posterior) portion 120 of the spinal cord 101, where the dorsal (or posterior) portion 120 of the spinal cord 101 can be identified via locating the posterior median sulcus 125. As shown, the epidural space 128 is positioned between the bone 129 (vertebrae) and the dura mater 115. Thus, electrical signals transmitted by the electrode 107 must be configured to pass through the dura mater 115, subdural cavity 113, arachnoid mater 114, subarachnoid cavity 130, and pia mater 127 to reach the target neural tissue, non-neural tissue, or a combination thereof 124 and deliver the desired electrical signals therein. By placing the electrode or electrodes 107 in the epidural space 128 adjacent a dorsal D (or posterior) portion 120 of the spinal cord 101, electrical signals can be delivered to target neural tissue, non-neural tissue, or a combination thereof 124 located within or adjacent a dorsal root ganglion 122 to provide therapy to the patient. Specific diseases or conditions that can be treated based on stimulation of the dorsal root ganglion include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, cervical neuritis, post herpetic neuralgia, vertigo, tinnitus, hearing loss and inflammatory pain such as arthritis, irritable bowel pain, osteoarthritis pain and fibromyalgia.

Figure 8:
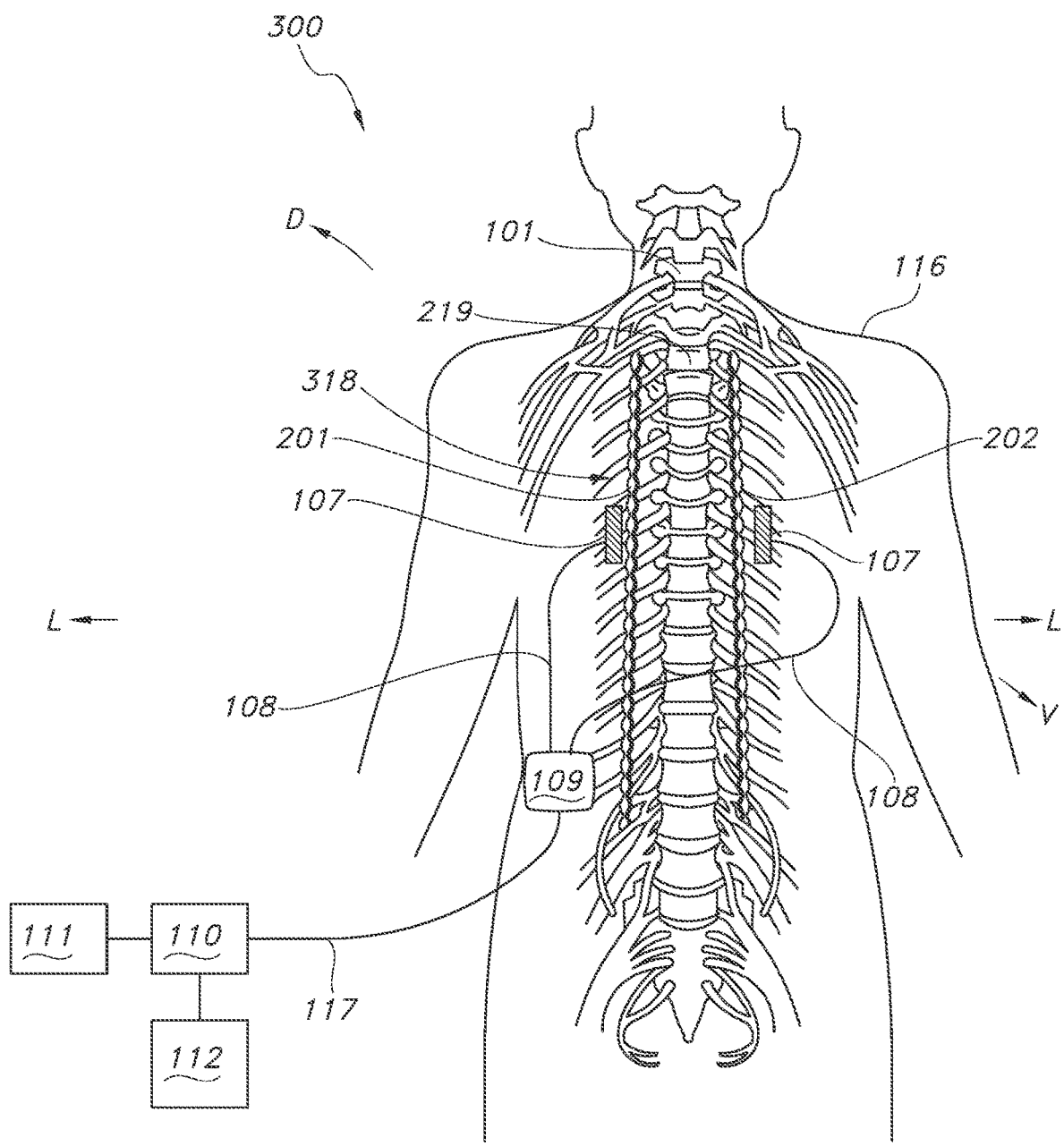
FIG. 8 illustrates at least one embodiment of a system for delivering one or more electrical signals to target neural tissue, non-neural tissue, or a combination thereof in a patient, where the electrical signals are adjustable, and where the target tissue is located within or adjacent a sympathetic chain ganglion.

Referring now to FIG. 8, there is illustrated a system 300 for delivering one or more electrical signals to provide therapy to a patient 116, where the target neural tissue, non-neural tissue, or a combination thereof 318 located adjacent a ventral or anterior region 219 of a spinal cord 101 of the patient 116. It should be appreciated that the system 300 of FIG. 8 may include similar elements and/or features to the system 50 described in reference to FIG. 1. In particular, the target neural tissue, non-neural tissue, or a combination thereof 318 can be a sympathetic chain ganglion located in the right sympathetic chain 201, the left sympathetic chain 202, or a combination thereof. As shown in FIG. 8, in some embodiments, the system 300 can include multiple devices to control and deliver electrical signals to an area within or adjacent target neural tissue, non-neural tissue, or a combination thereof 318 located adjacent a ventral V (or anterior) region 219 of the spinal cord 101 to provide therapy to the patient 116. In general, the system 300 of FIG. 8 can include one or more electrodes 107 (shown diagrammatically in FIG. 8 and not in any specific detail) that are connected by an electrical lead 108 to a signal generator 109. An additional lead 117 can be used to couple the signal generator 109 to the rest of the system 300, which can include a user interface 112, and a controller 110, where it is to be understood that as an alternative to the use of the lead 117, the signal generator 109 can be wirelessly connected to the rest of the system 50. The system may also include an isolated power system 111 and/or a patient monitor system. Further, it should be understood that while the system 300 of FIG. 8 illustrates a configuration where electrical signals can be delivered to target neural tissue, non-neural tissue, or a combination thereof utilizing an electrode or electrodes 107 coupled to an implantable signal generator 109 via a lead 108, the electrode or electrodes 107 can alternatively be coupled to an external signal generator via a wireless antenna system. Regardless, the electrode or electrodes 107 can be in the form of an electrode assembly that can that can deliver electrical signals to a patient to provide therapy to the patient and/or improve one or more of the patient's symptoms.

Figure 9:
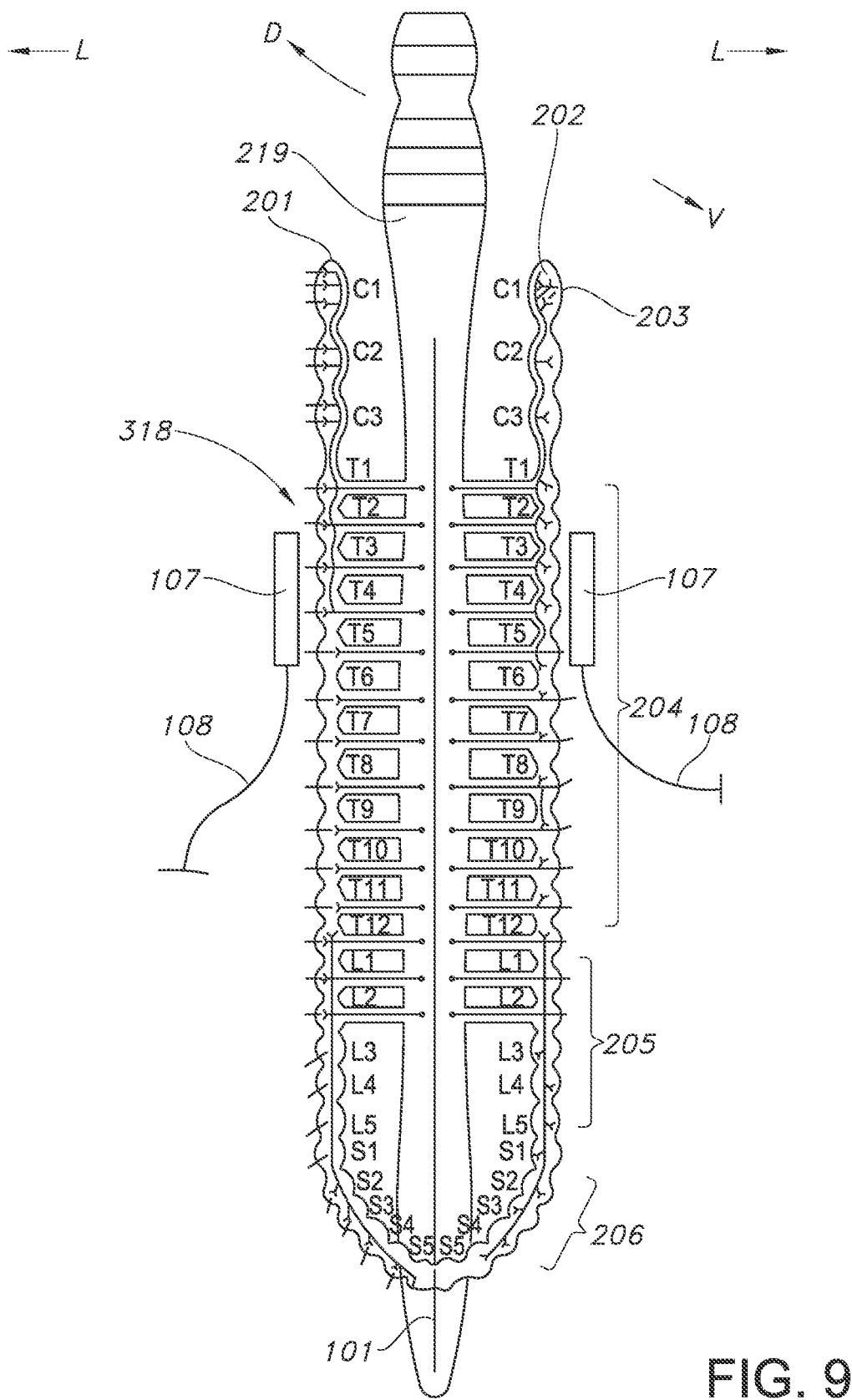
FIG. 9 is a zoomed-in view of the sympathetic chain and illustrates at least one option for electrode placement according to the system of FIG. 8.

Referring now to FIG. 9, the placement of the electrode or electrodes 107 is discussed in more detail. For instance, one or more electrodes 107 can be positioned adjacent a region of the right sympathetic chain 201 or the left sympathetic chain 202 of the patient 116, where the sympathetic chains 201 and 202 are located ventral and lateral to a ventral (or anterior) region 219 of the spinal cord 101. By placing the electrode or electrodes 107 adjacent target neural tissue, non-neural tissue, or a combination thereof 318 located lateral and ventral to a ventral (or anterior) region 219 of the spinal cord 101, one or more electrical signals can be delivered to the target neural tissue, non-neural tissue, or a combination thereof 318 (e.g., a ganglion or ganglia of the right sympathetic chain 201 or the left sympathetic chain 202) to provide therapy to the patient.

For instance, electrical signals can be delivered to a ganglion or ganglia associated with the cervical portion 203, the thoracic portion 204, the lumbar portion 205, or the sacral portion 206 of the right sympathetic chain 201 or the left sympathetic chain 202, or any combination thereof to provide therapy to the targeted area or areas. In one particular embodiment, an electrode 107 can be placed adjacent the cervical region 203 of the sympathetic chain to affect nerve fiber activity associated with levels C1-C3, which can affect nerve fiber activity associated with the eyes, the lachrymal glands, the salivary glands, and the sweat glands, hair follicles, and blood vessels of the head, neck, and arms. In another embodiment, an electrode 107 can be placed adjacent levels T1-T4 of the thoracic region 204, which can affect nerve fiber activity associated with the heart and lungs. In an additional embodiment, an electrode 107 can be placed adjacent levels T5-T9 of the thoracic region 204, which can affect nerve fiber activity associated with the stomach, duodenum, pancreas, liver, kidneys, and adrenal medulla. In yet another embodiment, an electrode 107 can be placed adjacent levels T10-T11 of the thoracic region 204, which can affect nerve fiber activity associated with the stomach and duodenum. In one more embodiment, an electrode 107 can be placed adjacent level T12 of the thoracic region 204 and levels L1-L3 of the lumbar region 205, which can affect nerve fiber activity in the colon, rectum, bladder, and external genitalia. In still another embodiment, an electrode 107 can be placed adjacent levels L4-L5 of the lumbar region 205 and levels S1-S3 of the sacral region 206, which can affect nerve fiber activity associated with the sweat glands, hair follicles, and blood vessels of the lower limbs. In another embodiment, an electrode 107 can be placed adjacent levels S4-S5 of the sacral region 206, which can affect nerve fiber activity associated with the sweat glands, hair follicles, and blood vessels of the perineum. Specific diseases or conditions that can be treated based on stimulation of a sympathetic nervous system include, for example, complex regional pain syndrome, peripheral vascular disease and chronic limb ischemia, angina pain, diabetic pain, abdominal/visceral pain syndrome, phantom limb pain, Raynaud's syndrome, diabetic peripheral neuropathy, hypertension, hypotension, headache and migraine, and inflammatory pain such as arthritis, irritable bowel pain, osteoarthritis pain, and fibromyalgia. It should be appreciated that, in some embodiments, the electrode(s) 107 may be placed beside other autonomic structures including parasympathetic nerves (e.g., vagus nerve).

Figure 10:
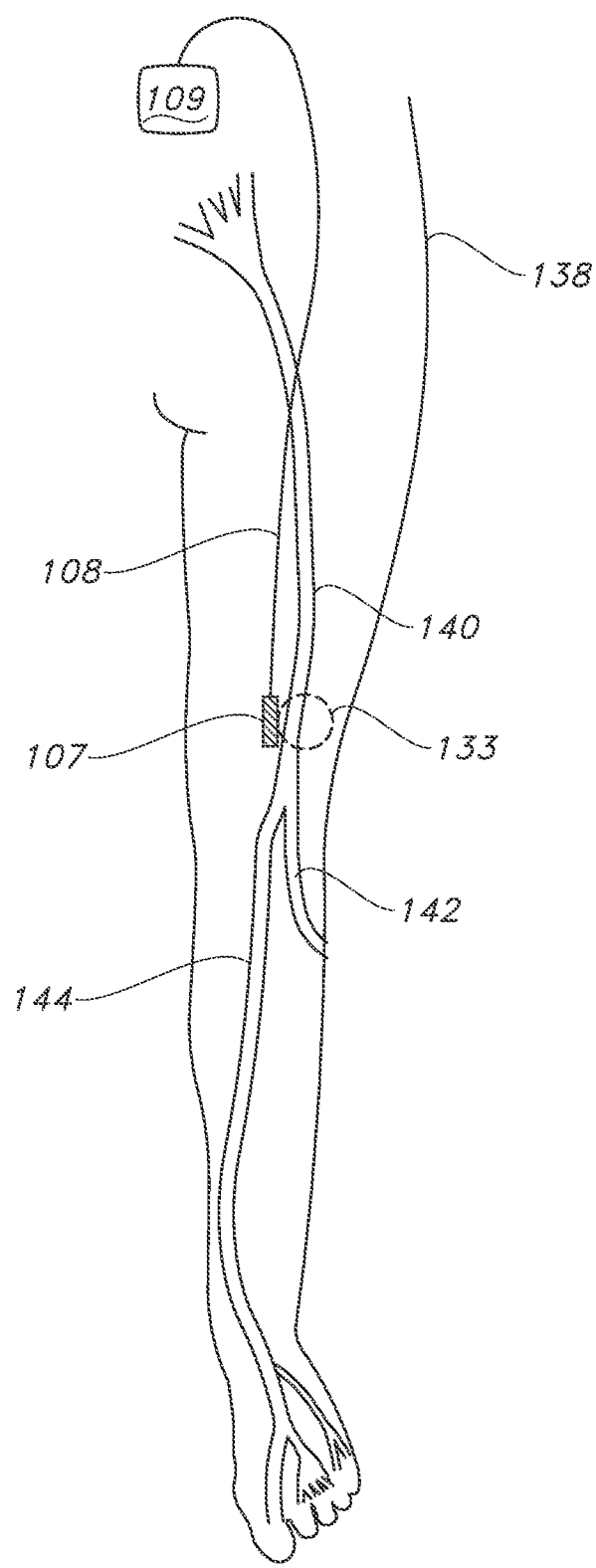
FIG. 10 illustrates at least one embodiment of a system for delivering one or more electrical signals to target neural tissue, non-neural tissue, or a combination thereof in a patient, where the electrical signals are adjustable, and where the target tissue is located within or adjacent a peripheral nerve.

Referring now to FIG. 10, the placement of the electrode or electrodes 107 in order to deliver one or more electrical signals to an area within or adjacent target neural tissue, non-neural tissue, or a combination thereof 133 located adjacent or near a peripheral nerve is discussed in more detail. For instance, one or more electrodes 107 can be positioned near or adjacent a peripheral nerve at any location along its length, where the peripheral nerve can run, for instance, down the length of the leg 138 of the patient 116. In the particular embodiment of FIG. 10, the target tissue 133 is located adjacent the sciatic nerve 140, although it is to be understood that neural tissue, non-neural tissue, or a combination thereof can be located adjacent any peripheral nerve in the leg (e.g., the common peroneal nerve 142, the tibial nerve 144, etc.), or any other location in the body. By placing the electrode or electrodes 107 adjacent or near a peripheral nerve, electrical signals can be delivered to the target neural tissue, non-neural tissue, or a combination thereof 133 to provide therapy to the patient. Specific diseases or conditions that can be treated based on stimulation of a peripheral nerve include, for example, acute pain, failed back surgery syndrome, complex regional pain syndrome, peripheral vascular disease and chronic limb ischemia, angina pain, diabetic pain, abdominal/visceral pain syndrome, brachial plexitis, phantom limb pain, intractable pain secondary to spinal cord injury, mediastinal pain, Raynaud's syndrome, headache and migraine, cervical neuritis, post-herpetic neuralgia, vertigo, tinnitus, hearing loss and inflammatory pain such as arthritis, irritable bowel pain, overactive bladder, bowel incontinence or constipation, osteoarthritis pain, and fibromyalgia. For example, electrical signals can be used to stimulate the sacral nerve roots to treat overactive bladder, fecal incontinence, and/or sexual dysfunction. In some embodiments, the electrode(s) may be placed adjacent or near a cranial nerve.

It should be appreciated from the description that the electrode(s) 107 may be placed in particular location in order to treat a particular condition using the adjustable random electrical stimulation technologies described herein. For example, in an embodiment, the electrode(s) 107 may be placed within an epidural space between T7 and T12 of a thoracic portion of the patient's spine to treat the patient for spinal lumbar pain. In another embodiment, the electrode(s) 107 may be placed within an epidural space between C2 and T1 of a cervical portion of the patient's spine to treat the patient for spinal cervical pain. In another embodiment, the electrode(s) 107 may be placed within an epidural space between C2 and T8 of the patient's spine to treat angina pain. In another embodiment, the electrode(s) 107 may be placed within an epidural space between C2 and T8 of the patient's spine to treat abdominal pain. In another embodiment, the electrode(s) 107 may be placed within an epidural space between T10 and L5 of the patient's spine to treat peripheral vascular disease. In another embodiment, the electrode(s) 107 may be placed within an epidural space between T7 and T12 in the thoracic spine to treat spinal lumbar pain disorders. In another embodiment, the electrode(s) 107 may be placed within an epidural space between C2 and T1 of a cervical portion of the patient's spine to treat the patient for upper limb ischemia. In another embodiment, the electrode(s) 107 may be placed at or within a dorsal root ganglion of the patient's spin to treat chronic or acute pain. In another embodiment, the electrode(s) 107 may be placed within a sacral portion of the patient's spine to treat urinary or fecal incontinence. In various embodiments, the electrode(s) 107 may be placed near or around the lumbar sympathetic plexus, the celiac sympathetic plexus, the hypogastric sympathetic plexus, or the stellate ganglion to treat chronic or acute pain of the limb, abdomen, pelvic area, or upper extremity, respectively. In another embodiment, the electrode(s) 107 may be placed near or around the patient's brain to treat movement disorders, Parkinson's, pain, psychiatric and/or seizure disorders. In another embodiment, the electrode(s) 107 may be placed near or around the patient's vagus nerve to treat seizure disorders, obesity, pain, or autonomic disorders. In another embodiment, the electrode(s) 107 may be placed near or around a peripheral nerve of the patient to treat acute pain, chronic pain, fecal or urinary incontinence, seizure disorders, movement disorders, obesity, spasticity, and to modulate other unpleasant neurological conditions. In another embodiment, the electrode(s) 107 may be placed near or around the patient's somatic tissue, muscles, connective tissue, or non-neural tissue to treat acute pain, chronic pain, fecal or urinary incontinence, seizure disorders, movement disorders, obesity, spasticity, and to modulate other unpleasant neurological conditions. In another embodiment, the electrode(s) 107 may be placed near or around the patient's visceral tissue or organs, and non-neural tissue to treat acute pain, chronic pain, fecal or urinary incontinence, seizure disorders, movement disorders, obesity, spasticity, and to modulate other unpleasant neurological conditions.

The various components of the systems 50, 100, and 300 described in FIGS. 1-10 may form the portion of an electrical stimulation system 400 as described below in more detail in reference to FIG. 11.

Figure 11:
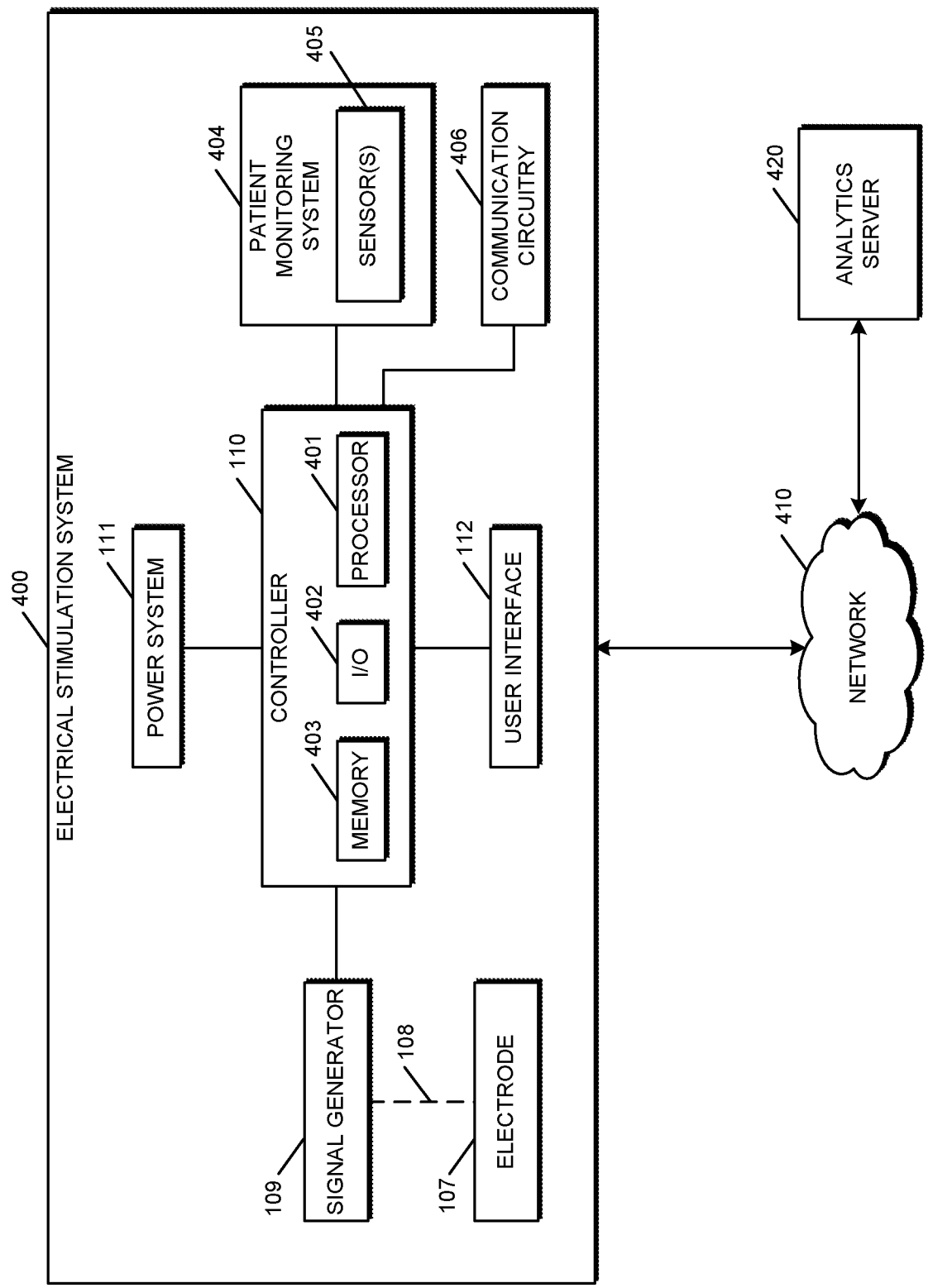
FIG. 11 is a simplified block diagram of at least one embodiment of an electrical stimulation system for providing therapy to a patient via the application of one or more adjustable electrical signals.

Referring now to FIG. 11, a simplified block diagram of at least one embodiment of an electrical stimulation system 400 for providing therapy to a patient via the application of one or more adjustable electrical signals and otherwise performing the functions described herein is shown. The illustrative electrical stimulation system 400 includes an electrode 107, a signal generator 109, a controller 110, a power system 111, a user interface 112, a patient monitoring system 404, and a communication circuitry 406. Further, in the illustrative embodiment, the controller 110 includes a processor 401, an input/output ("I/O") subsystem 402, and a memory 403, and the patient monitoring system 404 includes one or more sensors 405. It should be appreciated that one or more of the components of the electrical stimulation system 400 described herein may be embodied as, or form a portion of, one or more embedded controllers and/or integrated circuits. For example, in some embodiments, the processor 401, the I/O subsystem 402, the memory 403 and/or other components of the electrical stimulation system 400 may be embodied as, or form a portion of, a microcontroller or SoC (e.g., such as an embodiment in which the controller 110 is a microcontroller). Further, depending on the particular embodiment, the components of the electrical stimulation system 400 may be closely positioned to one another or spatially distributed (i.e., separated from one another) depending on the particular embodiment. Additionally, although only a single electrode 107, signal generator 109 controller 110, power system 111, user interface 112, patient monitoring system 404, communication circuitry 406, processor 401, I/O subsystem 402, and memory 403 are illustratively shown in FIG. 11, it should be appreciated that a particular electrical stimulation system 400 may include multiple electrodes 107, signal generators 109, controllers 110, power systems 111, user interfaces 112, patient monitoring systems 404, communication circuitries 406, processors 401, I/O subsystems 402, and/or memories 403 in various embodiments.

One or more electrodes 107 can be used to deliver the electrical signals to the target neural tissue, non-neural tissue, or a combination thereof as described herein. Depending on the particular embodiment, the one or more electrodes 107 can be implantable, percutaneous, or transcutaneous. Further, the one or more electrodes 107 can have a monopolar, bipolar, or multipolar configuration. For example, an electrode 107 used in a bipolar or multi-polar fashion has at least one cathode and one anode in the vicinity of the target neural tissue, non-neural tissue, or a combination thereof, while a monopolar electrode 107 can have a cathode located nearby the target neural tissue, non-neural tissue, or a combination thereof, and a return electrode 107 positioned some distance away. Further, the electrode 107 shape and size, and inter-electrode spacing can be specific to contouring the electrical field surrounding the target neural tissue, non-neural tissue, or a combination thereof, to enable specific therapy to be provided to the target neural tissue, non-neural tissue, or a combination thereof. It should be appreciated that one or more electrodes 107 may be embodied on or electrically coupled to one or more electrical leads 108, which may be connected to the signal generator 109 as described herein.

In some embodiments, the electrode 107 may contain a thermistor for recording tissue temperature during stimulation, and for providing feedback information for efficacy and safety measures, and temperature control. The electrode 107 may also be configured to measure tissue impedance for providing feedback information for efficacy and safety measures, and impedance control. Lastly, a cooling mechanism may be incorporated into the electrode design to control temperature at the electrode-tissue interface. In some embodiments, a single implantable electrode 107 with multiple large surface-area contacts will deliver large electric fields to target tissue in a bipolar fashion, and without exceeding tissue temperatures of 42° C., or impedance spikes reaching 50% above the baseline. Independent current channels, electrolytic jelly, and electrode insulation may be used to prevent co-excitation of surrounding tissue and to optimize the electrical field that is exposed to the nerve. The electrode 107 may be placed through a needle-like introducer assembly or applicator, and may include catheterover-needle or needle-over-catheter approaches where the catheter may include electrical contacts for delivery of the stimulation waveform. The position of specific geometric features of the electrode 107 (e.g. tip, side, different contacts, etc.) relative to the target structure may be optimized to provide the desired therapeutic effect with minimal undesired side-effects (such as co-excitation of nearby excitable tissues).

As shown in the figures, the electrode or electrodes 107 may be connected to an implantable signal generator 109 through an electrical lead 108. Alternatively, in some embodiments, the signal generator 109 can be external and can be wirelessly connected to the electrode or electrodes 107. In some embodiments, the signal generator 109 can be configured to generate and deliver electrical signals to provide therapy to a patient that can be customized based on patient feedback. As described above, the patient feedback may be based on self-report (e.g., introspection, observations of unwanted sensory- and/or motor activity, autonomic dysfunction, etc.), determined from data generated by sensors measuring physiological outcomes, based on data from artificial intelligence or machine learning systems (e.g., output or feedback data), or based on combinations thereof.

The use of multiple signal generators 109 (or multiple waveform generators) may enhance the resolution of the signal generator 109 by independently powering some electrical contacts with one signal, and powering other contacts with a different signal, and/or by allowing one waveform to be added to another waveform and delivered through the same set of contacts. Accordingly, an electrical stimulation system 400 that contains multiple independent signal generators 109 (or multiple waveform generators) may enable improved control of electrical contacts, may enable improved control of the waveform's randomness, and/or may facilitate interactions between frequency bands (e.g., multi-waveform, physiological, and psychophysical masking).

Regardless of the particular type or combination of electrical signals utilized, the electrical signals can be adjusted, such that the energy contained within a particular frequency band, and for all frequency bands of energy delivered to the tissue, can be adjusted to best treat the patient as described herein. In illustrative embodiments, the adjustable electrical energy can be adjusted to deliver electrical signals with intensities ranging from about 1 mA (or 0.1 mA) to about 100 mA and from about 1 V (or 0.1 V) to about 200 V (peak-to-peak) for each frequency band included in the spectrum. In illustrative embodiments, the spectrum of electrical signals includes frequencies ranging from about 0 Hz to about 100 kHz (or about 0 Hz to about 500 kHz), and is composed of adjustable frequency bands. It should be appreciated that the size of the frequency bands may vary depending on the particular embodiment (e.g., 10 Hz bands, 100 Hz bands, 1000 Hz bands, etc.). In some embodiments, the spectrum of electrical signals includes frequencies ranging from 0 Hz to 25 kHz (or about 0 Hz to about 25 kHz), and each of the frequency bands within the frequency range may have a bandwidth of 1 kHz or 2 kHz. In another embodiment, the spectrum of electrical signals includes frequencies ranging from about 0 Hz (e.g., 0.05 Hz) to 750 kHz. More specifically, in some embodiments, the spectrum of electrical signals may have a frequency range of about 0 Hz (e.g., 0.05 Hz) to about 2 kHz, which blocks the action potential from even firing, and/or each of the frequency bands within the frequency range may have a bandwidth of about 150 Hz or about 200 Hz. In another embodiment, the spectrum of electrical signals may have a frequency range of 10 kHz to 16 kHz, which stimulates the nerve so that it attenuates or prevents the nerve from firing a pain signal. In yet another embodiment, the spectrum of electrical signals may have a frequency range of 500 kHz to 750 kHz, which results in so much energy around the nerve that it causes the nerve cell to run out of its mitochondrial stores of energy. In other words, such electrical stimulation signals may fatigue the nerve, so that it essentially becomes tired and is unable to fire. As such, the electrical stimulation system 400 is able to deliver the signals to the patient for a period (e.g., five minutes), turn the stimulation off for an extended period (e.g., several days) while the nerve cells rebuild their mitochondrial stores, and again deliver the signals to the patient to again fatigue the nerve and deplete the stores. It has been discovered that delivering the electrical stimulation signals within this frequency range for approximately five minutes may block the nerve for approximately twenty-one days. Accordingly, it should be appreciated that the mechanism of action of the electrical stimulation signals that are delivered to the patient may vary depending on the particular frequency range of the signals. In alternative embodiments, the spectrum of electrical signals may have a frequency range of 1 kHz to 100 kHz, or the spectrum of electrical signals may have a frequency range of 100 kHz to 1 MHz. It should be appreciated that the frequency range of 100 kHz to 1 MHz may selectively inhibit the parts of the nerve responsible for normal pain and autonomic function. The time-course of these effects have been demonstrated to last days-to-weeks (e.g., 21 days post-treatment) when healthy neuronal circuitry is simulated, and weeks-to-months when stimulation is delivered to diseased neural circuitry (e.g., hosting chronic pain). Although various frequency ranges are described herein as being "from about 0 Hz," it should be appreciated that such lower bound may be some non-zero frequency greater than 0 Hz in some embodiments (e.g., 0.05 Hz, 0.1 Hz, 1 Hz, etc.). Moreover, the frequency band that receives power can be determined in a random fashion.

The power supply, power source, or power system 111 is configured to supply power to the controller 110 and/or other components of the electrical stimulation system 400. In some embodiments, the power system 111 is an independent, untethered, and portable power source configured to supply power to the electrical stimulation system 400 to perform the various functions described herein. For example, the power system 111 may include one or more batteries, battery packs, capacitors, super capacitors, solar cells, and/or other power supplies. Depending on the particular embodiment, the power system 111 may or may not be rechargeable. In other embodiments, the power system 111 may be line powered via AC mains and/or another suitable power source. It should be appreciated that the power system 111 can include both external and internal portions, where the internal portion of the power system can include a battery, such as a lithium battery, and the external portion of the power system 111 can be plugged into a wall and used to recharge the battery as needed. In such embodiments, the external portion of the power system 111 can transmit power to the signal generator 109 as directed by the controller 110 via RF signals/electromagnetic induction, or power can be transmitted to the signal generator 109 via the battery in the internal portion of the power system 111. Further, the external portion of the power system 111 can be used to recharge the battery in the internal portion of the power system 111.

The user interface 112 may be embodied as any one or more devices or components that allow a user to interact with the electrical stimulation system 400. For example, in some embodiments, the user interface 112 can be in the form of a computer that interacts with the controller 110 and is powered by a power system 111. In particular, in some embodiments, the computer can operate software designed to record signals passed from the controller 110, and to drive the controller's output. Possible software packages include Cambridge Electronic Design's (UK) SPIKE program. The software can be programmable and can record and analyze electrophysiological signals, as well as direct the controller 110 to deliver the electrical signals described herein. Further, in some embodiments, the user interface 112 may include one or more peripheral devices such as, for example, a keyboard, mouse, display, status indicator, diagnostic tool, speaker, microphone, and/or one or more other suitable peripheral devices.

In some embodiments, the electrical stimulation system 400 may include a patient monitoring system 404. In such embodiments, the patient monitoring system 404 can acquire, amplify/attenuate, and filter physiological signals and then output them to the controller 110. It should be appreciated that the patient monitoring system 404 may include one or more sensors 405. The sensors 405 are configured to generate sensor data (e.g., by virtue of one or more signals), which may be interpreted by the controller 110 (e.g., the processor 401) to determine one or more characteristics associated with the patient and/or the electrical stimulation system 400. By way of example, the sensors 405 may detect various characteristics of the physical environment of the electrical stimulation system 400 (internal and/or external) and/or other suitable characteristics. In various embodiments, the sensors 405 may be embodied as, or otherwise include, environmental sensors, inertial sensors, proximity sensors, optical sensors, electromagnetic sensors, audio sensors, pressure sensors, flow meters, temperature sensors, thermistors, chemical sensors, biopotential electrodes, motion sensors, piezoelectric sensors, cameras, and/or other types of sensors. Of course, the electrical stimulation system 400 may also include components and/or devices configured to facilitate the use of the sensors 405. For example, in some embodiments, the patient monitoring system 404 may include a heart-rate monitor to collect electrocardiogram signals and/or a muscle activity monitor to collect electromyography signals. The heart-rate monitor can include ECG electrodes coupled with an alternating current (AC) amplifier, and the muscle activity monitor can include EMG electrodes coupled with an AC amplifier. Other types of transducers may also be used in other embodiments. As described, physiological signals obtained with the patient monitoring system 404 may be passed through an AC signal amplifier/conditioner. One possible amplifier/conditioner is a Model LP511 AC amplifier available from Grass Technologies, a subsidiary of Astro-Med, Inc., West Warwick, Rhode Island, USA.

The communication circuitry 406 may be embodied as any communication circuitry, transceiver, device, or collection thereof, capable of enabling communications between the electrical stimulation system 400 and other remote devices. The communication circuitry 406 may be configured to use any one or more wired and/or wireless communication technologies and associated protocols. For example, in some embodiments, the illustrative electrical stimulation system 400 may be configured to communicate via Wi-Fi (e.g., infrastructure or ad hoc mode), Wi-Fi Direct, Bluetooth (including Bluetooth Low Energy (BLE)), Zig-bee, Z-wave, Near Field Communication (NFC), IEEE 802.15, and/or other suitable wireless communication protocol(s). Further, in some embodiments, the electrical stimulation system 400 may be configured to communicate via Ethernet, Power over Ethernet (PoE), serial communication links, power line communication, and/or another suitable wired communication mechanism.

The controller 110 may be embodied as any type of controller or control system capable of performing the functions described herein. In the illustrative embodiment, the controller 110 can record electrical signal data as well as digital information from the patient monitoring system 404, and can generate electrical signal and digital outputs simultaneously for real-time control of the signal generator 109 based on feedback received from the patient after transmission of the electrical stimulation signals. The controller 110 may have onboard memory to facilitate high speed data capture, independent waveform sample rates, and on-line analysis. An exemplary controller 110 may be a POWER 1401 data-acquisition interface unit available from Cambridge Electronic Design (UK).

As shown, in some embodiments, the controller 110 includes a processor 401, an I/O subsystem 402, and memory 403.

The processor 401 may be embodied as any type of processor(s) capable of performing the functions described herein. In particular, the processor 401 may be embodied as one or more single or multi-core processors, microcontrollers, or other processor or processing/controlling circuits. For example, in some embodiments, the processor 401 may include or be embodied as an arithmetic logic unit (ALU), central processing unit (CPU), digital signal processor (DSP), and/or another suitable processor(s). The processor 401 may be a programmable type, a dedicated hardwired state machine, or a combination thereof. One or more processors 401 with multiple processing units may utilize distributed, pipelined, and/or parallel processing in various embodiments. Further, the processor 401 may be dedicated to performance of just the operations described herein, or may be utilized in one or more additional applications. In the illustrative embodiment, the processor 401 is of a programmable variety that executes algorithms and/or processes data in accordance with operating logic as defined by programming instructions (such as software or firmware) stored in the memory 403. Additionally or alternatively, the operating logic for the processor 401 may be at least partially defined by hardwired logic or other hardware. Further, the processor 401 may include one or more components of any type suitable to process the signals received from input/output devices or from other components or devices and to provide desired output signals. Such components may include digital circuitry, analog circuitry, or a combination thereof.

The memory 403 may be of one or more types of non-transitory computer-readable media, such as a solid-state memory, electromagnetic memory, optical memory, or a combination thereof. Furthermore, the memory 403 may be volatile and/or nonvolatile and, in some embodiments, some or all of the memory 403 may be of a portable variety, such as a disk, tape, memory stick, cartridge, and/or other suitable portable memory. In operation, the memory 403 may store various data and software used during operation of the electrical stimulation system 400 such as operating systems (e.g., real-time operating systems (RTOS)), applications, programs, libraries, and drivers. The memory 403 is communicatively coupled to the processor 401 via the I/O subsystem 402, which may be embodied as circuitry and/or components to facilitate input/output operations with the processor 401, the memory 403, and other components of the electrical stimulation system 400. For example, the I/O subsystem 402 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. Depending on the particular embodiment, the memory 403 may be included with the processor 401 and/or coupled to the processor 401 depending on the particular embodiment. For example, in some embodiments, the processor 401, the I/O subsystem 402, the memory 403, and/or other components of the electrical stimulation system 400 may form a portion of a system-on-a-chip (SoC) and be incorporated on a single integrated circuit chip.

As shown in FIG. 11, in some embodiments, the electrical stimulation system 400 or a portion thereof (e.g., the controller 110) may be configured to communicate with an analytics server 420 and/or other remote computing device via a network 410. For example, in some embodiments, the electrical stimulation system 400 may transmit patient data (e.g., including optimal electrical stimulation signature), sensor data, and/or other data to the analytics server 420 for leveraging artificial intelligence, machine learning, and/or other technologies for pattern identification and/or decision-making.

The network 410 may be embodied as any type of communication network capable of facilitating communication between the electrical stimulation system 400 and the analytics server 420 and/or other remote devices. As such, the network 410 may include one or more networks, routers, switches, computers, and/or other intervening devices. For example, the network 410 may be embodied as or otherwise include one or more cellular networks, telephone networks, local or wide area networks, publicly available global networks (e.g., the Internet), ad hoc networks, short-range communication links, or a combination thereof.

The analytics server 420 may be embodied as any type of device(s) capable of performing the functions described herein. It should be appreciated that the efficacy of neuromodulation technologies is affected by continuously changing treatment variables. Treatment variables may be device-specific (e.g., lead migration and impedance changes, stimulation paradigm, etc.), physiological (e.g., neurological conditioning or tolerance, scar tissue formation, plasticity, etc.), psychological (e.g., depression, etc.), disease state specific (e.g., progression, improvement, etc.) and/or patient dependent (e.g., height, weight, age, race, etc.). Moreover, these treatment variables generally change with time and may interact (stim*time interaction, long-term physiological changes, etc.).

The term "tunable electrical stimulation signature" or "adjustable electrical stimulation signature" may be used herein to describe the optimal (or best-known) stimulation paradigm used by a patient to maximize treatment efficacy. In some embodiments, one or more artificial intelligence and/or machine learning algorithms/technologies may be leveraged to help patients determine and maintain the proper adjustable electrical stimulation signature throughout the life of the patients' respective treatments. Accordingly, it should be appreciated that the electrical stimulation system 400 may be configured to export the adjustable electrical stimulation signature (e.g., after identifying the signature) and various treatment variables for one or more patients (e.g., each patient) to the analytics server 420 and/or another system/device. In some embodiments, the analytics server 420 may collect the adjustable electrical stimulation signature and treatment variables from many electrical stimulation systems 400, and use artificially intelligent processes (e.g., machine learning, deep learning, neural networks, and/or other technologies) to predict a novel adjustable electrical stimulation signature. The predicted adjustable electrical stimulation signature (re-adjusted signature) may then be transmitted back to one or more electrical stimulation systems 400 to be installed and trailed by one or more patients. Further, in some embodiments, the patient may then accept or modify the stimulation paradigm as necessary to best treat their condition in a manner similar to the adjusting of electrical stimulation signals otherwise described herein. It should be appreciated that the prediction may help to program the electrical stimulation system 400 initially, may be used over time to optimize treatment, and/or may be used to re-capture a failing therapy. Moreover, in some embodiments, the artificial intelligence programs may also be used to predict entirely new treatments for novel indications.

In some embodiments, the inputs for a neural network or other machine learning algorithm used by the analytics server 420 may include one or more of adjusted electrical stimulation signatures, patient information, patient demographics, diagnosis information, electrode positioning, patient sensations, measures of treatment efficacy and/or outcomes (e.g., Pain Rating Scale scores), time of day, duration of treatment, time elapsed since start of treatment plan, and/or other machine learning model inputs. Further, in various embodiments, the analytics server 420 may utilize any machine learning and/or artificial intelligence algorithm for performing the functions described herein. For example, in some embodiments, the analytics server 420 may utilize one or more neural network algorithms, regression algorithms, instance-based algorithms, regularization algorithms, decision tree algorithms, Bayesian algorithms, clustering algorithms, association rule learning algorithms, deep learning algorithms, dimensionality reduction algorithms, and/or other suitable machine learning algorithms, techniques, and/or mechanisms.

It should be further appreciated that, although the analytics server 420 is described herein as a computing device outside of a cloud computing environment, in other embodiments, the analytics server 420 may be embodied as a cloud-based device or collection of devices within a cloud computing environment. Further, in cloud-based embodiments, the analytics server 420 may be embodied as a server-ambiguous computing solution, for example, that executes a plurality of instructions on-demand, contains logic to execute instructions only when prompted by a particular activity/trigger, and does not consume computing resources when not in use. That is, the analytics server 420 may be embodied as a virtual computing environment residing "on" a computing system (e.g., a distributed network of devices) in which various virtual functions (e.g., Lambda functions, Azure functions, Google cloud functions, and/or other suitable virtual functions) may be executed corresponding with the functions of the analytics server 420 described herein. For example, when an event occurs (e.g., data is transferred to the analytics server 420 for handling), the virtual computing environment may be communicated with (e.g., via a request to an API of the virtual computing environment), whereby the API may route the request to the correct virtual function (e.g., a particular server-ambiguous computing resource) based on a set of rules. For example, when a request for the transmission of data is made (e.g., via an appropriate user interface to the analytics server 420), the appropriate virtual function(s) may be executed to perform the actions before eliminating the instance of the virtual function(s).

Figure 12:
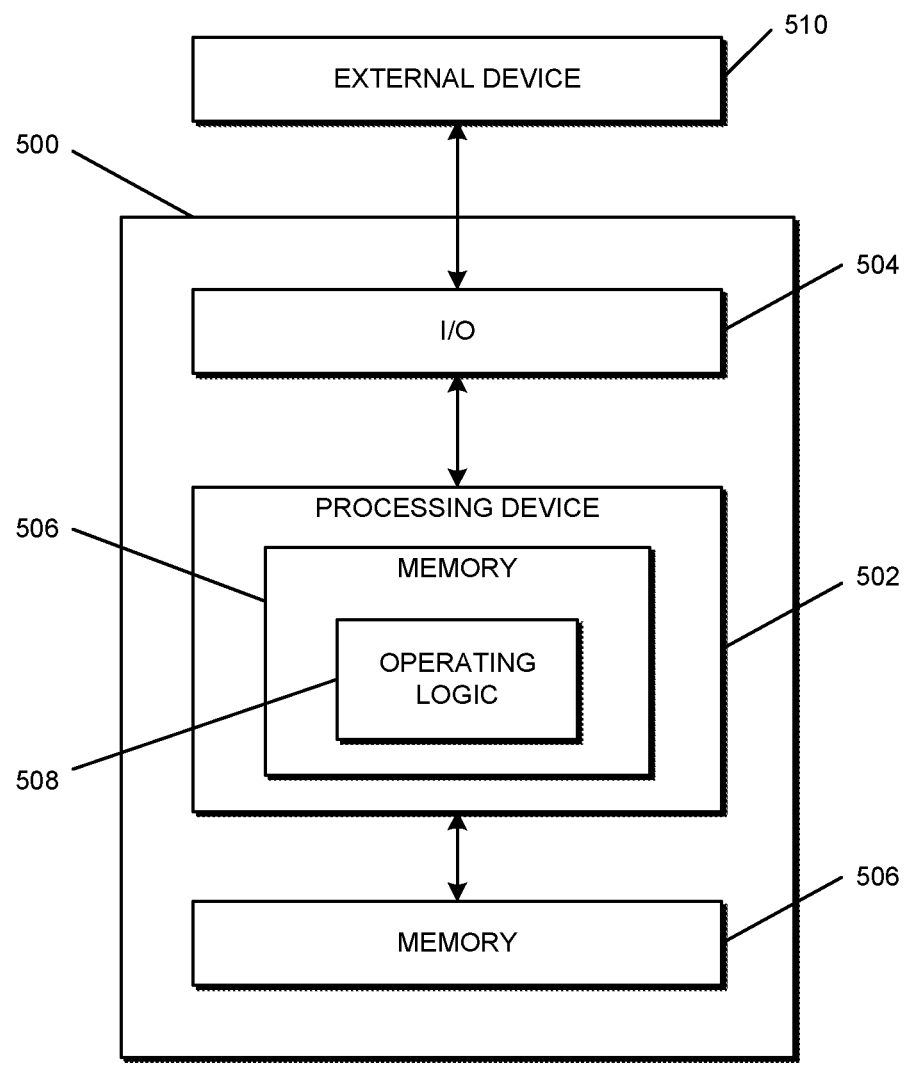
FIG. 12 is a simplified block diagram of at least one embodiment of a computing system.

Referring now to FIG. 12, a simplified block diagram of at least one embodiment of a computing device 500 is shown. The illustrative computing device 500 depicts at least one embodiment of a server that may be utilized in connection with the analytics server 420 illustrated in FIG. 12 and/or other devices in communication with the electrical stimulation system 400. Depending on the particular embodiment, the computing device 500 may be embodied as a server, desktop computer, laptop computer, tablet computer, notebook, netbook, Ultrabook™, mobile computing device, cellular phone, smartphone, wearable computing device, personal digital assistant, Internet of Things (IoT) device, processing system, router, gateway, and/or any other computing, processing, and/or communication device capable of performing the functions described herein.

The computing device 500 includes a processing device 502 that executes algorithms and/or processes data in accordance with operating logic 508, an input/output device 504 that enables communication between the computing device 500 and one or more external devices 510, and memory 506 which stores, for example, data received from the external device 510 via the input/output device 504.

The input/output device 504 allows the computing device 500 to communicate with the external device 510. For example, the input/output device 504 may include a transceiver, a network adapter, a network card, an interface, one or more communication ports (e.g., a USB port, serial port, parallel port, an analog port, a digital port, VGA, DVI, HDMI, FireWire, CAT 5, or any other type of communication port or interface), and/or other communication circuitry. Communication circuitry of the computing device 500 may be configured to use any one or more communication technologies (e.g., wireless or wired communications) and associated protocols (e.g., Ethernet, Bluetooth®, Wi-Fi®, WiMAX, etc.) to effect such communication depending on the particular computing device 500. The input/output device 504 may include hardware, software, and/or firmware suitable for performing the techniques described herein.

The external device 510 may be any type of device that allows data to be inputted or outputted from the computing device 500. For example, in various embodiments, the external device 510 may be embodied as the analytics server 420 and/or the electrical stimulation system 400. Further, in some embodiments, the external device 510 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 510 may be integrated into the computing device 500.

The processing device 502 may be embodied as any type of processor(s) capable of performing the functions described herein. In particular, the processing device 502 may be embodied as one or more single or multi-core processors, microcontrollers, or other processor or processing/controlling circuits. For example, in some embodiments, the processing device 502 may include or be embodied as an arithmetic logic unit (ALU), central processing unit (CPU), digital signal processor (DSP), and/or another suitable processor(s). The processing device 502 may be a programmable type, a dedicated hardwired state machine, or a combination thereof. Processing devices 502 with multiple processing units may utilize distributed, pipelined, and/or parallel processing in various embodiments. Further, the processing device 502 may be dedicated to performance of just the operations described herein, or may be utilized in one or more additional applications. In the illustrative embodiment, the processing device 502 is programmable and executes algorithms and/or processes data in accordance with operating logic 508 as defined by programming instructions (such as software or firmware) stored in memory 506. Additionally or alternatively, the operating logic 508 for processing device 502 may be at least partially defined by hardwired logic or other hardware. Further, the processing device 502 may include one or more components of any type suitable to process the signals received from input/output device 504 or from other components or devices and to provide desired output signals. Such components may include digital circuitry, analog circuitry, or a combination thereof.

The memory 506 may be of one or more types of non-transitory computer-readable media, such as a solid-state memory, electromagnetic memory, optical memory, or a combination thereof. Furthermore, the memory 506 may be volatile and/or nonvolatile and, in some embodiments, some or all of the memory 506 may be of a portable type, such as a disk, tape, memory stick, cartridge, and/or other suitable portable memory. In operation, the memory 506 may store various data and software used during operation of the computing device 500 such as operating systems, applications, programs, libraries, and drivers. It should be appreciated that the memory 506 may store data that is manipulated by the operating logic 508 of processing device 502, such as, for example, data representative of signals received from and/or sent to the input/output device 504 in addition to or in lieu of storing programming instructions defining operating logic 508. As shown in FIG. 12, the memory 506 may be included with the processing device 502 and/or coupled to the processing device 502 depending on the particular embodiment. For example, in some embodiments, the processing device 502, the memory 506, and/or other components of the computing device 500 may form a portion of a system-on-a-chip (SoC) and be incorporated on a single integrated circuit chip.

In some embodiments, various components of the computing device 500 (e.g., the processing device 502 and the memory 506) may be communicatively coupled via an input/output subsystem, which may be embodied as circuitry and/or components to facilitate input/output operations with the processing device 502, the memory 506, and other components of the computing device 500. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing device 500 may include other or additional components, such as those commonly found in a typical computing device (e.g., various input/output devices and/or other components), in other embodiments. It should be further appreciated that one or more of the components of the computing device 500 described herein may be distributed across multiple computing devices. In other words, the techniques described herein may be employed by a computing system that includes one or more computing devices. Additionally, although only a single processing device 502, I/O device 504, and memory 506 are illustratively shown in FIG. 12, it should be appreciated that a particular computing device 500 may include multiple processing devices 502, I/O devices 504, and/or memories 506 in other embodiments. Further, in some embodiments, more than one external device 510 may be in communication with the computing device 500.

Figure 13:
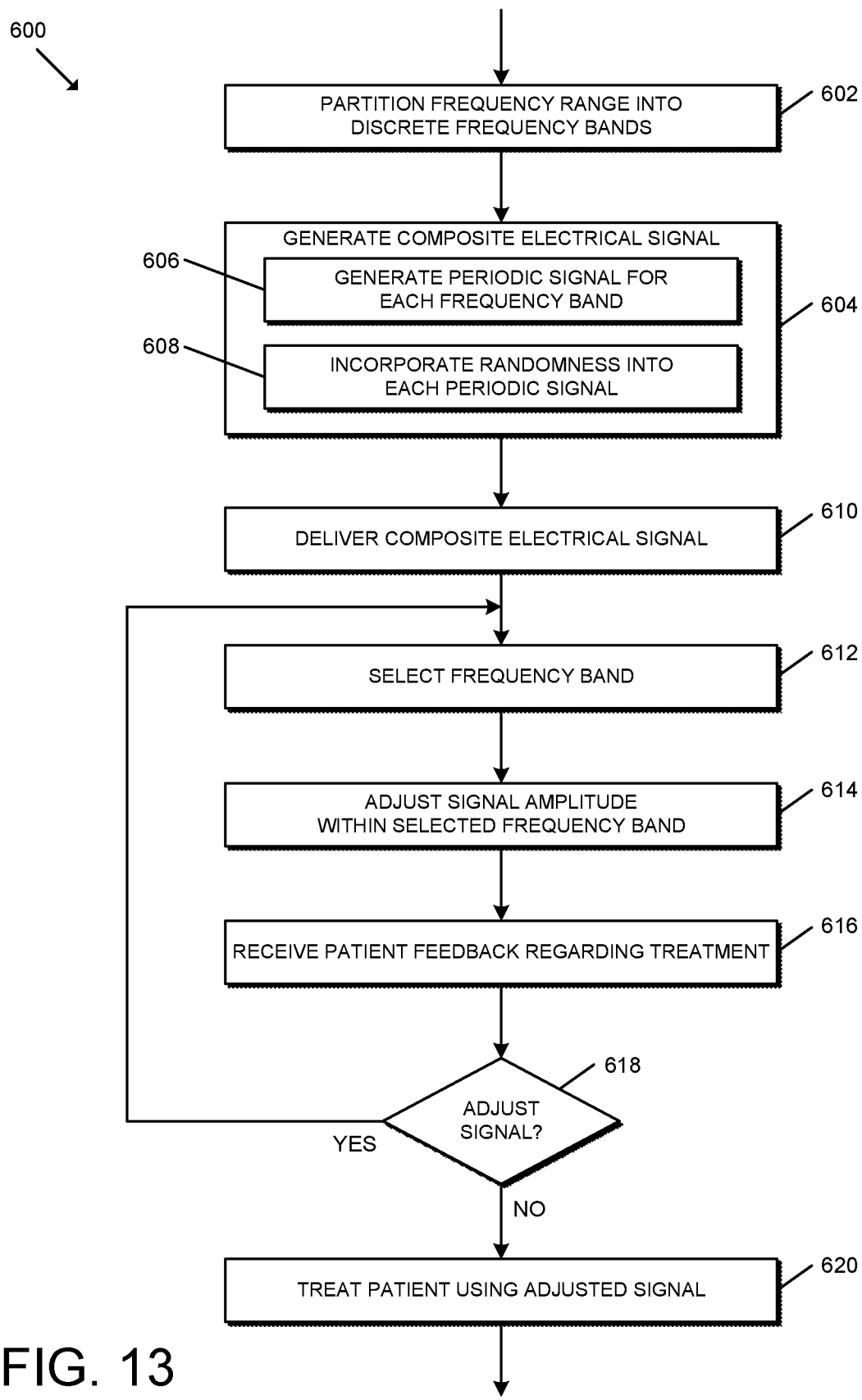
FIG. 13 is a simplified flow diagram of at least one embodiment of a method for providing therapy to a patient via the application of one or more adjustable electrical signals.

Referring now to FIG. 13, in use, the electrical stimulation system 400 may execute a method 600 for providing therapy to a patient via the application of one or more adjustable electrical signals. It should be appreciated that the particular blocks of the method 600 are illustrated by way of example, and such blocks may be combined or divided, added or removed, and/or reordered in whole or in part depending on the particular embodiment, unless stated to the contrary.

Figure 14:
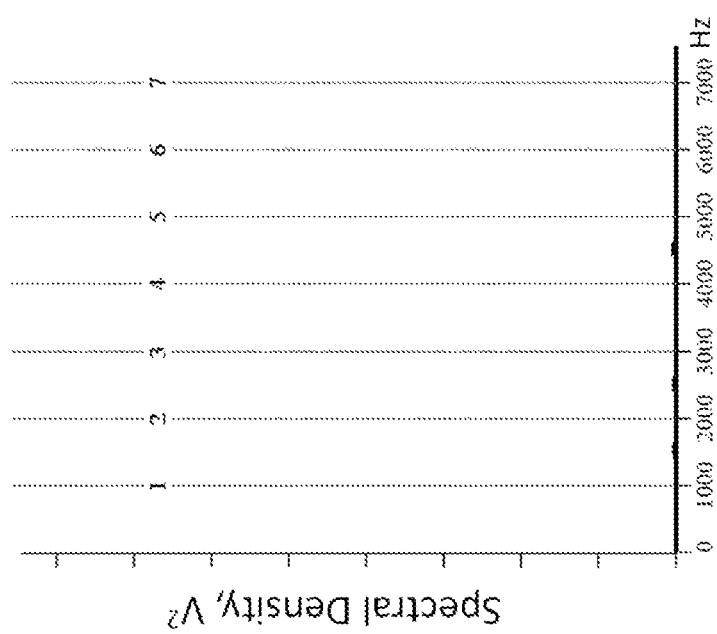
FIG. 14 is a graph that illustrates partitioned frequency bands of at least a portion of a frequency range of an electrical signal.

The illustrative method 600 begins with block 602 in which the electrical stimulation system 400 (e.g., the controller 110) partitions a frequency range into discrete frequency bands. For example, in an embodiment, the frequencies range may be from 0 to 100,000 Hz in equally spaced linear frequency bands (e.g., 1,000 Hz, 2,500 Hz, etc.). By way of example, FIG. 14 depicts a frequency range that is partitioned into discrete frequency bands that have 1,000 Hz bandwidths. In an embodiment, each of the frequency bands in a frequency range of 0 Hz to 100 kHz of the partitioned spectrum has a bandwidth of one of 1 kHz or 2 kHz. Accordingly, it should be appreciated that the size of the bandwidths may different depending on the particular embodiment. Additionally, the bandwidths may have the same or different widths depending on the particular embodiment. In some embodiments, the frequency may be described on a logarithmic scale and described by base2 (e.g., octaves: 10 Hz, 20 Hz, 40 Hz, 80 Hz, 160 Hz, 320 Hz, 640 Hz, 1280 Hz, 2560 Hz, etc.) and/or base-10 (e.g., 10 Hz, 100 Hz, 1,000 Hz, 10,000 Hz, 100,000 Hz, etc.) axis, with bandwidths described a Q-factor (center frequency/bandwidth) or bandwidth: octaves (1/10 to 10 oct).

In block 604, the electrical stimulation system 400 (e.g., the signal generator 109) generates a composite electrical signal to be delivered through one or more electrodes 107 to the patient based on a plurality of electrical signals (e.g., an electrical signal for each frequency band in the frequency range or spectrum). It should be appreciated that the composite electrical signal may be generated based on the plurality of electrical signals as a sum of the periodic signals (e.g., as a Fourier series) and/or using other techniques consistent with the features described herein. In generating the composite signal, in block 606, the electrical stimulation system 400 (e.g., the signal generator 109) may generate a separate periodic signal for each frequency band in the frequency range. In particular, in some embodiments, the electrical stimulation system 400 may generate a sinusoidal waveform for each frequency band that has a frequency within that respective frequency band. For example, a sinusoidal waveform for a 1-2 kHz frequency band would have a frequency of 1-2 kHz, and a sinusoidal waveform for a 3-4 kHz frequency band would have a frequency of 3-4 kHz.

In block 608, the electrical stimulation system 400 (e.g., the signal generator 109) may incorporate randomness into each periodic signal. For example, for a sinusoidal waveform within a 1-2 kHz frequency band, the electrical stimulation system 400 may randomize the frequency of oscillation within that frequency band such that the frequency is not a constant value (between 1-2 kHz) but has a frequency that varies over time (i.e., the frequency randomly changes within the 1-2 kHz range). It should be appreciated that the electrical stimulation system 400 may incorporate randomness into the corresponding periodic signal using any suitable random generator, noise generator, random process, or other technology capable of adding variability to the signal within the bandwidth as described herein. For example, in some embodiments, the randomness is incorporated into the corresponding periodic signal by virtue of a random number generator that drives the phase and/or frequency (period) of a particular bandwidth within a set of limits. For example, suppose a therapeutic frequency range is divided into ten bandwidths with ten sinusoidal waveforms used to fill the frequency space, and further that one of the bandwidths ranges from 10 kHz to 12 kHz. The sinusoid used to fill that bandwidth may be randomly varied in frequency between 10 kHz and 12 kHz, which could be done by using a random number generator to adjust the period of the waveform between 0.083 ms and 0.1 ms. Although randomness is primarily described herein as being incorporated by virtue of randomness in the frequency of oscillation within the respective frequency bands, it should be appreciated that the system may, additionally or alternatively, incorporate randomness into the periodic signal(s) by randomizing the amplitude of the periodic signal(s) within the corresponding bandwidth and/or randomizing the corresponding phase of the periodic signal(s). In some embodiments, randomness may be incorporated across multiple parameters simultaneously (e.g., frequency, amplitude, and/or phase).

Figure 15:
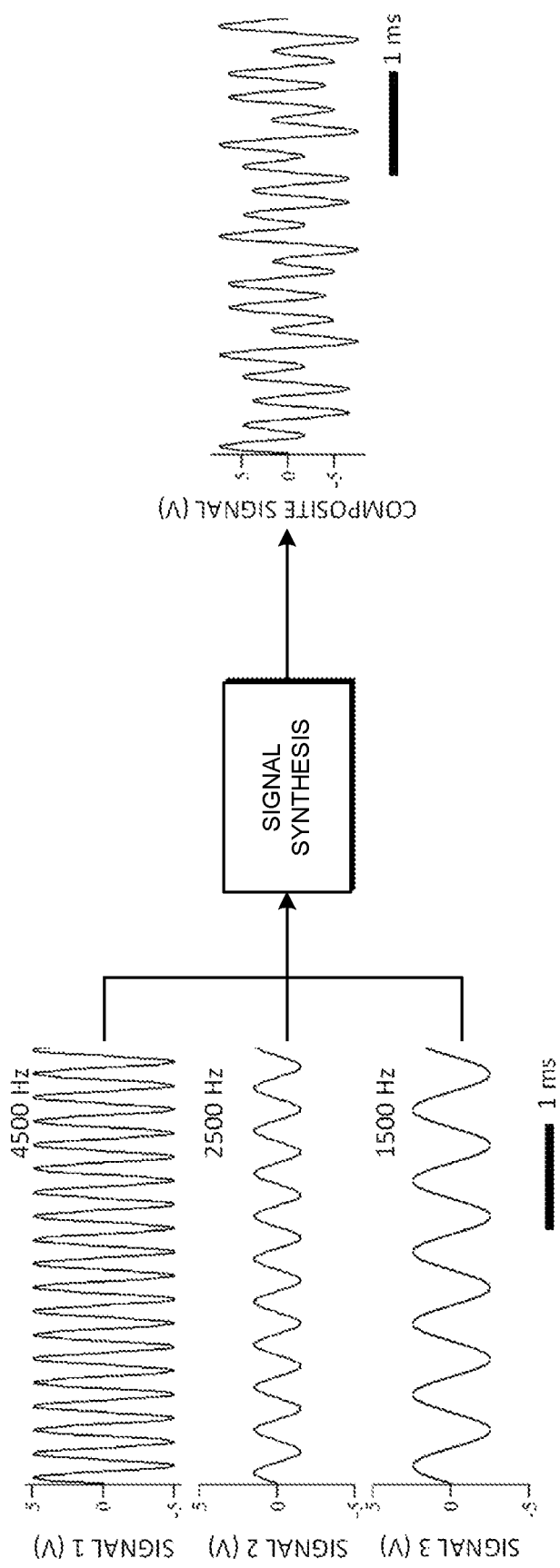
FIG. 15 is a simplified diagram that illustrates at least one embodiment of generating a composite electrical signal.
Figure 17:
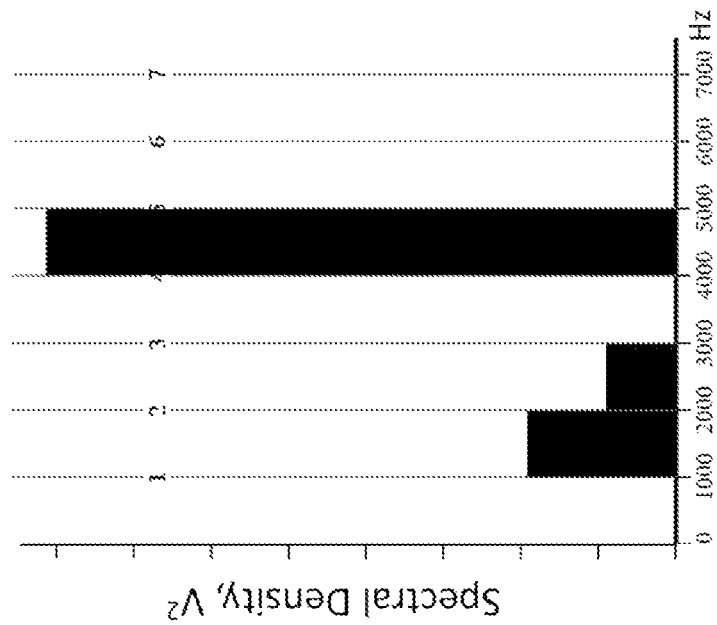
FIG. 17 is a graph of the power spectrum of a composite signal composed of the three particular sinewaves when each sinewave randomly varies its frequency within its respective frequency band.
Figure 16:
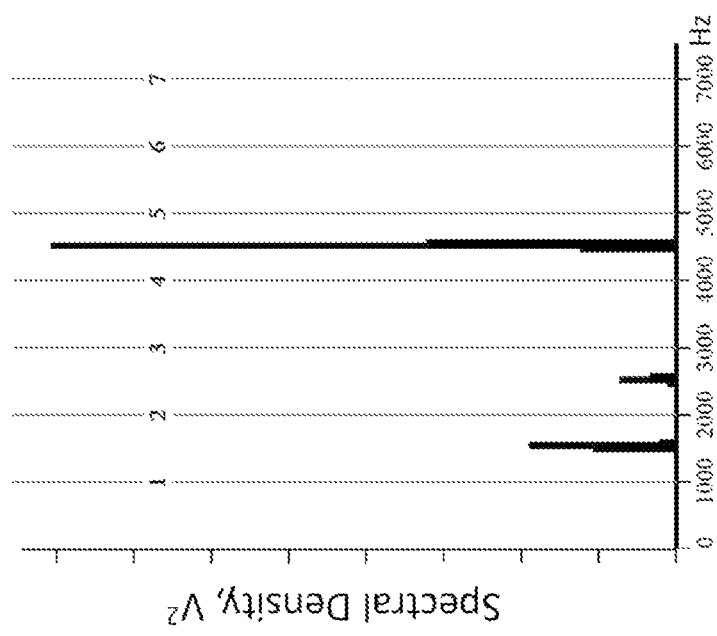
FIG. 16 is a graph of the power spectrum of a composite signal composed of three particular sinewaves.

By way of example, FIG. 15 illustrates three sinusoidal signals that are synthesized into a composite signal using the techniques described herein. In particular, in the illustrative embodiment, the first sinusoidal waveform has a frequency of 4500 Hz and an amplitude of 5 V, the second sinusoidal waveform has a frequency of 2500 Hz and an amplitude of 1.5 V, and the third sinusoidal waveform has a frequency of 1500 Hz and an amplitude of 2.5 V. The composite signal generated in FIG. 15 has no randomness incorporated, and the power spectrum of the composite signal is depicted in FIG. 16. However, if the frequency of each of the three sinusoidal waveforms is allowed to randomly vary within the respective frequency bands (i.e., the partitions), the composite signal would have a power spectrum as depicted in FIG. 17.

Although described as using a sinusoid, it should be appreciated that the electrical stimulation system 400 may utilize other types of periodic waveforms in other embodiments. For example, in some embodiments, one or more of the periodic signals may be embodied as a square wave signal, a triangle wave signal, a saw tooth wave signal, and/or another type of periodic signal. However, in such embodiments, it should be appreciated that the corresponding periodic signal may include components outside of the corresponding frequency bandwidth. Accordingly, in such embodiments, the electrical stimulation system 400 may include filtration circuitry, software, and/or components configured to filter out the components outside of the corresponding frequency bandwidth.

For example, the electrical stimulation system 400 (e.g., the signal generator 109 and/or the controller 110) may include a filter bank that includes one or more bandpass filters. that cumulatively cover the entire frequency range. Further, in some embodiments, the controller 110 may control the filter bank to modify each bandpass filter's operational settings including, for example, center frequency, cutoff frequencies (e.g., half-power points), attenuation rate (filter-order), overall attenuation of the passband, and/or other operational settings of the filter. The signals outputted from each bandpass filter may be passed through an amplifier, which may be controlled by the controller 110 to apply gain to the corresponding filtered signals based on the patient feedback described below, and compiled into a single electrical waveform (e.g., the tuned/adjusted electrical signal).

In block 610, the electrical stimulation system 400 (e.g., the signal generator 109) delivers the composite electrical signal through one or more electrodes 107 to the patient in order to treat the patient. In block 612, the electrical stimulation system 400 selects a particular frequency band of the discretely partitioned frequency bands for adjustment. In particular, in some embodiments, selection of the particular frequency band may involve selecting the corresponding signal generator 109 (in the case of multiple signal generators 109) or a particular periodic waveform generator (e.g., within a singular signal generator 109). In block 614, the electrical stimulation system 400 adjusts the amplitude of the voltage and/or current of the signal within the selected frequency band, for example, by amplifying the voltage and/or current of the signal within that particular frequency band or attenuating the voltage and/or current of the signal within that particular frequency band. It should be appreciated that the amount of amplification/attenuation of the signal may be user-controlled, predefined, and/or otherwise determined depending on the particular embodiment. It should be appreciated that, in the illustrative embodiment, the clinician and/or patient may select and/or adjust the frequency band using one or more user interface 112 devices. However, the frequency band may be otherwise selected in other embodiments. In other embodiments, the electrical stimulation system 400 may additionally or alternatively adjust the phase and/or frequency of the periodic waveform corresponding with the selected frequency band in order to tune the patient.

In block 616, the electrical stimulation system 400 and/or the clinician receives feedback regarding the treatment from the patient. As described above, it should be appreciated that the feedback can be provided by the patient, for example, based on self-report (e.g., introspection, observations of unwanted sensory- and/or motor activity, autonomic dysfunction, etc.), determined from data generated by sensors measuring physiological outcomes, based on data from artificial intelligence or machine learning systems (e.g., output or feedback data), or based on combinations thereof. In block 618, the electrical stimulation system 400 and/or the clinician determines whether to further adjust the signal applied to the patient based on the patient feedback (e.g., in an effort to most optimally alleviate the patient's condition). If so, the method 600 returns to block 612 in which the electrical stimulation system 400 selects a frequency band for further adjustment (e.g., the same frequency band for further modification, or a different frequency band for modification). If not, the method 600 advances to block 620 in which the patient is further treated using the adjusted signal, which was adjusted for optimal (or improvement) treatment of the patient's condition. In some embodiments, the adjusted signal may be delivered to the patient continuously or intermittently (e.g., with durations of less than thirty minutes).

Although the blocks 602-620 are described in a relatively serial manner, it should be appreciated that various blocks of the method 600 may be performed in parallel in some embodiments.

It should be appreciated that, in some embodiments, bursts of periodic or aperiodic signals may be delivered simultaneously with the adjusted composite signal described herein. The signals may be delivered through the same electrodes 107 as the adjusted composite signal or may be delivered through a different set of electrodes 107 depending on the particular embodiment. The signals may include pulses, sinewaves, sawtooth waveforms, or any other periodic waveforms. It should be appreciated that aperiodic signals include noise, impulses, transients, or any other aperiodic waveforms. The signal parameters (amplitude, frequency, pulse width, inter-pulse interval, burst time, inter-burst frequency, etc.) of the periodic and aperiodic signals may be informed by patient feedback, including those used to adjust the composite signal. Moreover, in some embodiments, the bursts of periodic and aperiodic signals may occur randomly, even during times when the adjusted composite signal is not being delivered.

What is claimed is:

1. A method for providing therapy to a patient, the method comprising:
    partitioning a frequency range into a plurality of discrete frequency bands, each of the discrete frequency bands having a corresponding bandwidth, wherein the frequency range is 0 Hz to 2 kHz, and each of the discrete frequency bands in the frequency range of 0 Hz to 2 kHz has a bandwidth of 200 Hz;
    generating, by at least one signal generator controlled by a controller of an electrical stimulation system, a composite electrical signal based on a plurality of periodic signals, wherein each periodic signal has a frequency within a corresponding frequency band of the plurality of discrete frequency bands;
    delivering the composite electrical signal through one or more electrodes to the patient to target at least one of neural tissue or non-neural tissue of the patient;
    adjusting an amplitude of one or more of a voltage or a current of the composite electrical signal within a selected frequency band of the plurality of discrete frequency bands to generate an adjusted electrical signal based on feedback received from the patient; and
    delivering the adjusted electrical signal through the one or more electrodes to provide therapy to the patient.

2. The method of claim 1, wherein generating the composite electrical signal based on the plurality of periodic signals comprises incorporating randomness into one or more of the plurality of periodic signals.

3. The method of claim 2, wherein incorporating randomness into one or more of the plurality of periodic signals comprises randomizing a corresponding frequency of each of the plurality of periodic signals within the corresponding bandwidth.

4. The method of claim 2, wherein incorporating randomness into one or more of the plurality of periodic signals comprises randomizing a corresponding amplitude of each of the plurality of periodic signals within the corresponding bandwidth.

5. The method of claim 2, wherein incorporating randomness into one or more of the plurality of periodic signals comprises randomizing a corresponding phase of each of the plurality of periodic signals within the corresponding bandwidth.

6. The method of claim 1, wherein each of the plurality of periodic signals comprises a sinusoidal waveform.

7. The method of claim 1, wherein generating the composite electrical signal based on the plurality of periodic signals comprises generating the composite electrical signal as a Fourier series based on the plurality of periodic signals.

8. The method of claim 1, wherein generating the composite electrical signal based on the plurality of periodic signals comprises applying filtration to each of the plurality of periodic signals.

9. The method of claim 1, wherein adjusting the amplitude of the one or more of the voltage or current of the composite electrical signal within the selected frequency band comprises amplifying the amplitude of the one or more of the voltage or current of the composite electrical signal within the selected frequency band.

10. The method of claim 1, wherein adjusting the amplitude of the one or more of the voltage or current of the composite electrical signal within the selected frequency band comprises attenuating the amplitude of the one or more of the voltage or current of the composite electrical signal within the selected frequency band.

11. The method of claim 1, wherein adjusting the amplitude of the one or more of the voltage or current of the composite electrical signal within the selected frequency band comprises adjusting the amplitude of the one or more of the voltage or current of the composite electrical signal within a first frequency band of the plurality of discrete frequency bands to generate a first adjusted electrical signal based on first feedback received from the patient; and further comprising adjusting an amplitude of the one or more of the voltage or current of the adjusted electrical signal within a second frequency band of the plurality of discrete frequency bands to generate a second adjusted electrical signal based on second feedback received from the patient.

12. The method of claim 1, wherein the feedback received from the patient is patient self-report regarding the therapy delivered to the patient.

13. The method of claim 1, wherein the feedback is based on data generated by one or more sensors of the electrical stimulation system, wherein the one or more sensors measure one or more physiological outcomes of the patient.

14. The method of claim 1, wherein the feedback comprises data received from a machine learning system.

15. The method of claim 14, further comprising executing the machine learning algorithm to identify an adjusted electrical stimulation signal to be delivered through the one or more electrodes to provide therapy to the patient based on a plurality of machine learning inputs.

16. The method of claim 15, wherein the machine learning inputs comprise one or more of adjusted electrical stimulation signatures, patient information, patient demographics, diagnosis information, electrode positioning, patient sensations, measure of treatment efficacy or outcomes, time of day, duration of treatment, or time elapsed since start of treatment plan.

17. The method of claim 1, further comprising placing the one or more electrodes on the patient percutaneously or transcutaneously.

18. The method of claim 1, wherein at least one of the one or more electrodes is implantable.

* * * * *